United States Patent [19]

Baldwin

[11] Patent Number: 4,567,276

[45] Date of Patent: Jan. 28, 1986

[54] β-ADRENERGIC 2-[4-(3-AMINO-2-HYDROXYPROPOXY)-PHENYL]IMIDAZOLES

[75] Inventor: John J. Baldwin, Gwynedd Valley, Pa.

[73] Assignee: Merck & Co., Inc., Rahway, N.J.

[21] Appl. No.: 503,923

[22] Filed: Jun. 13, 1983

Related U.S. Application Data

[60] Division of Ser. No. 255,202, Apr. 20, 1981, Pat. No. 4,440,774, which is a continuation-in-part of Ser. No. 184,501, Sep. 5, 1980, abandoned, which is a continuation of Ser. No. 801,120, May 27, 1977, abandoned, which is a continuation of Ser. No. 641,420, Dec. 17, 1975, Pat. No. 4,134,983, which is a continuation-in-part of Ser. No. 554,372, Mar. 3, 1975, abandoned.

[51] Int. Cl.[4] .................. C07D 233/64; C07D 233/68; C07D 233/90; C07D 401/04

[52] U.S. Cl. .......................................... 548/343; 544/3; 544/55; 544/56; 544/58.5; 544/63; 544/96; 544/98; 544/238; 544/333; 544/405; 546/167; 546/278; 548/205; 548/214; 548/235; 548/236; 548/247; 548/336; 548/337; 548/346

[58] Field of Search ............... 548/337, 336, 343, 346, 548/205, 214, 235, 236, 247; 546/278, 210, 167; 544/3, 55, 56, 58.5, 63, 96, 98, 238, 333, 405

[56] References Cited

PUBLICATIONS

Stuart, *Chem. Abst.* 74, 22855n (1970).

*Primary Examiner*—Richard A. Schwartz
*Assistant Examiner*—Kurt G. Briscoe
*Attorney, Agent, or Firm*—Alice O. Robertson; Salvatore C. Mitri

[57] ABSTRACT

Novel substituted imidazoles and methods for their preparation are disclosed. These imidazoles, and their salts, exhibit pharmacological activity which includes antihypertensive activity and β-adrenergic blocking activity.

15 Claims, No Drawings

β-ADRENERGIC 2-[4-(3-AMINO-2-HYDROXYPROPOXY)PHENYL-]IMIDAZOLES

BACKGROUND OF THE INVENTION

This is a division of application Ser. No. 255,202, filed Apr. 20, 1981 now U.S. Pat. No. 4,440,774, which is a continuation-in-part of copending application Ser. No. 184,501 filed Sept. 5, 1980, now abandoned, which is a continuation of U.S. application Ser. No. 801,120, filed on May 27, 1977, now abandoned, which in turn is a continuation of U.S. application Ser. No. 641,420 filed Dec. 17, 1975 now U.S. Pat. No. 4,134,983 issued Jan. 16, 1979 which in turn is a continuation-in-part of application Ser. No. 554,372 filed Mar. 3, 1975, now abandoned.

The present invention involves novel imidazoles which have antihypertensive and β-adrenergic blocking activity.

Various chemical agents are available for treating hypertension in man and animals. Certain trifluoromethyl imidazoles are known to have substantial antihypertensive activity. These imidazoles are disclosed in U.S. Pat. No. 3,786,061.

Another class of agents known as β-adrenergic blocking agents, are also available. These β-blocking agents affect cardiac, vascular and pulmonary functions and can be mild antihypertensives. Specifically, these agents have the capability of reducing heart rate, counteracting vasodepression and suppressing bronchodilation. β-adrenergic blocking agents, their chemical structure and activity, are disclosed in "Clinical Pharmacology and Therapeutics" 10, 292-306 (1969). Various β-adrenergic blocking agents are also described in the following patents: U.S. Pat. No. 3,048,387; U.S. Pat. No. 3,337,628; U.S. Pat. No. 3,655,663; U.S. Pat. No. 3,794,650; U.S. Pat. No. 3,832,470; U.S. Pat. No. 3,836,666; U.S. Pat. No. 3,850,945; U.S. Pat. No. 3,850,946; U.S. Pat. No. 3,850,947; U.S. Pat. No. 3,852,291 and British No. 1,194,548.

Where an antihypertensive agent acts principally via vasodilation, it may cause undesirable side effects such as substantially increased heart rate (tachycardia).

Novel imidazoles characterized by having amino-substituted propoxyaryl substitution have been discovered. These imidazoles have unexpected antihypertensive activity and β-adrenergic blocking activity.

SUMMARY OF THE INVENTION

Novel imidazoles having amino substituted propoxy aryl substitution and salts thereof; their preparation; pharmaceutical composition containing said imidazoles; and method of treatment of animals e.g. those having hypertension or angina pectoris, using said imidazoles.

DESCRIPTION OF PREFERRED EMBODIMENTS

An embodiment of the present invention is compounds having the formula

I

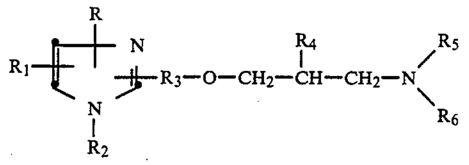

wherein $R$ and $R_1$ are independently selected from hydrogen, $C_1$-$C_{10}$ alkyl, substituted $C_1$-$C_{10}$ alkyl having 1-3 substituents, cycloalkyl, aryl, substituted aryl having 1-5 substituents, heterocyclic group having 5-6 ring atoms, halogen, cyano, carboxy and carboxy derivatives and

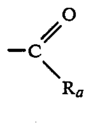

wherein $R_a$ is H or $C_1$-$C_6$ alkyl, $R_2$ is selected from hydrogen, $C_1$-$C_{10}$ alkyl, hydroxy-$C_1$-$C_{10}$-alkyl and $C_3$-$C_6$ alkenyl, $R_3$ is selected from aryl having 6 ring atoms of which 0-2 are non-carbon, substituted aryl having 1-4 substituents, fused ring aryl having 9-10 ring atoms of which 0-2 are non-carbon, and substituted fused ring aryl having 1-4 substituents, $R_4$ is selected from hydroxy and

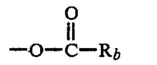

wherein $R_b$ is $C_1$-$C_6$ alkyl, and $R_5$ and $R_6$ when separate, are independently selected from hydrogen, $C_1$-$C_6$ alkyl and substituted $C_1$-$C_6$ alkyl having 1-3 substituents and, when joined, form a 5-6 membered N-alicyclic ring and pharmacologically acceptable acid addition and quaternary ammonium salts thereof.

Compounds of particular interest have the formulae:

IA

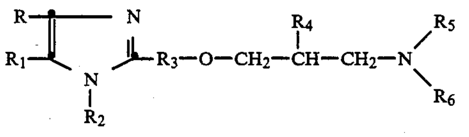

IB

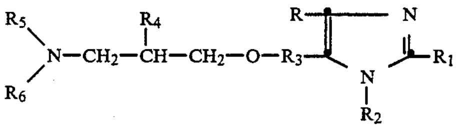

Useful $R$ and $R_1$ alkyl groups include unsubstituted as well as substituted alkyl, cycloalkyl as well as branched and linear alkyl groups. These alkyl groups may contain up to 10 alkyl carbons, preferably up to 8 alkyl carbon atoms and more preferably from 1 to 6 alkyl carbons. Examples of suitable $R$ and $R_1$ unsubstituted alkyl groups are methyl, isopropyl, cyclopropyl, cyclopentyl, 2-methyl-n-butyl, decyl, 2-ethyl-n-hexyl; suitable R and $R_1$ substituted alkyl groups have 1-3 substituents such as halo (Cl,Br,I,F) hydroxy, phenyl, $C_1$-$C_4$ alkoxy,-exemplified by $-CCl_3$, bromohexyl, $CH_3—O—CH_2—CH_2—$, hydroxypropyl, diiodethyl, trifluoromethyl, benzyl, chlorodecyl and the like.

Useful R and $R_1$ aryl groups include aryl groups having up to 10 ring carbon atoms. These aryl groups include single ring as well as fused ring aryls, unsubstituted aryls as well as substituted aryls having from 1-5 substituents. These substituents include alkyl, preferably $C_1$-$C_6$ alkyl, alkoxy preferably $C_1$-$C_6$ alkoxy, cyano, halo (Cl, I, Br and F), nitro, amino, carboxy, hydroxy, —SH, sulfamoyl, alkylthio, phenyl and the like. Examples of suitable aryl R and $R_1$ groups are phenyl, chlorophenyl, dibromophenyl, fluorophenyl, toluyl, xylyl, hexylphenyl, dodecylphenyl, tert-butylphenyl, methoxyphenyl, $C_6H_{13}$-O-phenyl, $HO—C_6H_4—$, carboxyphenyl, $$H-\overset{O}{\overset{\|}{C}}-C_6H_4,$$

sulfamoylphenyl, N,N-dimethylsulfamoylphenyl, naphthyl, indanyl, chloronaphthyl, triclorophenyl, $HO—CH_2—C_6H_4—$, pentafluorophenyl, the tetralin group, cyanophenyl, chlorohydroxyphenyl, $C_1$-$C_6$-alkyl-S-$C_6H_4$-,

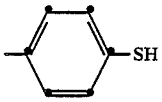

and the like.

Useful R and $R_1$ heterocyclic groups have 5-6 ring atoms of which 1-3 and preferably 1-2 are hetero atoms and the quinolyl group. Substituted as well as unsubstituted heterocyclic groups are included. The hetero atoms are O,S and N. Examples of suitable R and $R_1$ heterocyclic groups are pyridyl, pyrazinyl, pyrimidinyl, pyridazinyl substituted pyridyl such as dimethylpyridyl, methylpyridyl, chloropyridyl, dichloropyridyl, diethylpyridyl, trimethylpyridyl, methylethylpyridyl, ethylpyridyl, bromopyridyl, and analogous substituted pyrazinyl, pyrimidinyl and pyridazinyl groups; pyridyl-N-oxide, methylpyridyl-N-oxide, furyl, thienyl and the like.

Other useful R and $R_1$ groups are cyano, carboxy, carboxy derivatives such as $$-\overset{O}{\overset{\|}{C}}-O-C_1-C_6-alkyl,\ -\overset{O}{\overset{\|}{C}}-NH_2,$$

N-mono-$C_1$-$C_6$-alkyl- and N,N-di-$C_1$-$C_6$-alkylcarbamoyl; halogen preferably Br, Cl and F; and $$-\overset{O}{\overset{\|}{C}}-R_a$$

wherein $R_a$ is hydrogen or $C_1$-$C_6$ alkyl and the like.

It is preferred that at least one of R and $R_1$ is hydrogen.

Useful $R_2$ alkyl groups have up to 10 carbons, are unsubstituted or monohydroxysubstituted and include cycloalkyl as well as branched and straight chain alkyl. $R_2$ alkyl groups having 1-6 carbons are preferred, with 1-4 carbon atoms more preferred. Examples of suitable $R_2$ alkyl groups are methyl, ethyl, decyl, tert-butyl, isopropyl, 2,2,4-trimethyl-n-butyl, cyclohexyl, 2-hydroxyethyl, 3-hydroxypropyl, 2-hydroxybutyl and the like. Useful $R_2$ alkenyl groups have 3-6 carbon atoms and are exemplified by allyl, $—CH_2—CH_2—CH_2—CH—CH═CH_2$ and the like.

Preferred compounds are those where $R_2$ is H.

$R_3$ is an aryl group. The aryl group includes single ring (6-ring atoms) and fused ring (9-10 ring atoms) groups, having 0-2 nitrogen ring atoms, both substituted as well as unsubstituted moieties. The $R_3$ heterocyclic groups contain 1 or 2 nitrogen atoms. Examples of such useful heterocyclic groups are 2-pyridyl, 3-pyridyl, 4-pyridyl, halopyridyl, $C_1$-$C_3$ alkylpyridyls, pyridyl-N-oxides, cyanopyridyl, pyrazinyl, pyridazinyl, pyrimidinyl, and quinolyl, and the like. Preferred $R_3$ heterocyclic groups are pyridyl, substituted pyridyl e.g. chloropyridyl, methylethylpyridyl, methylpyridyl, 2-chloro-4-methylpyridyl, bromopyridyl, 2,4,6-trimethylpyridyl, dimethylpyridyl, and the N-oxides e.g. pyridyl-N-oxide, methylpyridyl-N-oxide and the like.

Useful $R_3$ carbocyclic aryl groups include phenyl groups and fused ring groups such as naphthyl, tetrahydronaphthyl, indanyl and the like.

Preferred $R_3$ carbocyclic aryl groups are those having the formula

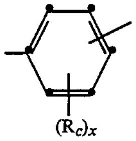

II where x is 0, 1,2,3, or 4 and $R_c$ includes alkyl groups, both linear and branched, and preferably $C_1$-$C_4$ alkyl groups, $C_3$-$C_6$ cycloalkyl groups, halogen such as Cl, I, Br or F, alkoxy preferably $C_1$-$C_4$ alkoxy, hydroxy, nitro, cyano, carbamoyl, N-$C_1$-$C_6$-alkyl- and N,N-di-$C_1$-$C_6$-alkylcarbamoyl, and the like. Examples of suitable preferred carbocyclic aryl groups of Formula II are phenyl, tetrahydronaphthyl, fluorophenyl, dibromophenyl, trichlorophenyl, iodophenyl, hydroxyphenyl, toluyl, cresyl, nitrophenyl, carboxyphenyl, methoxyphenyl, cyclohexylphenyl, aminophenyl, dimethylchlorophenyl, butoxyphenyl, dichlorophenyl, cyanophenyl, nitrophenyl, tetramethylphenyl, dimethylphenyl, carbamoylphenyl, N,N-dimethylcarbamoylphenyl and the like.

An especially preferred $R_3$ group is the carbocyclic group having the formula

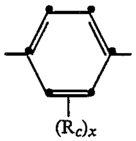

IIA

A more preferred $R_3$ carbocyclic group is formula II A where x is 0, 1, 2 or 3. An especially preferred carbocyclic $R_3$ group is formula II A where x is 0, 1 or 2. A most preferred carbocyclic group is

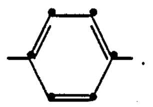

$R_4$ includes the hydroxy group and the ester group

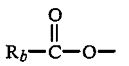

where $R_b$ is $C_1$–$C_6$ alkyl such as methyl, isopropyl, tert-butyl, hexyl, ethyl and the like. Compounds where $R_4$ is OH are preferred.

The $R_5$ and $R_6$ groups are hydrogen or alkyl groups. The alkyl groups preferably have from 1-6 alkyl carbon atoms and may be branched, linear, or cyclic; substituted or unsubstituted. Examples of suitable alkyl groups are methyl, n-hexyl, isopropyl, 2,2,4-trimethyl-n-butyl, cyclopropyl, cyclohexyl, chlorobutyl, tert-butyl,

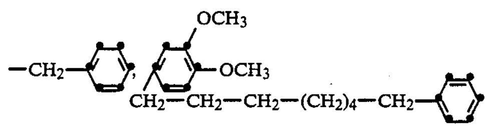

and the like. The $R_5$ and $R_6$ groups may also be joined to form a 5-6 membered N-alicyclic ring such as

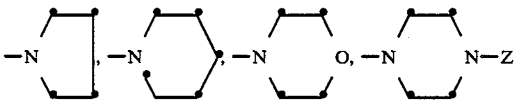

where Z is H or $C_1$–$C_{10}$ alkyl, and the like.

It is preferred that one of $R_5$ and $R_6$ is hydrogen while the other is $C_1$–$C_6$ alkyl, and preferably $C_3$–$C_4$ branched hydrocarbon alkyl.

Compounds of formula I which are preferred are those in which R is hydrogen, represented by the formula

III

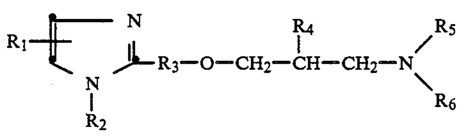

Another series of preferred compounds is that in which R and $R_2$ are each hydrogen. These compounds have the formula

IV

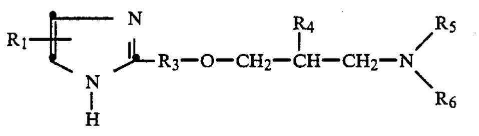

When $R_2$ is hydrogen, the 4 and 5 positions in the imidazole are substantially equivalent.

A more preferred series of compounds is that of formula IV where $R_1$ is selected from hydrogen, trihaloalkyl, preferably —$CF_3$, cyano, —$CH_3$, phenyl, substituted phenyl having 1-5 substituents preferably selected from halogen (Cl, Br, F), and heterocyclic group such as thienyl, furyl, methylpyridyl, pyridyl, pyridyl-N-oxide and the like.

Another more preferred series of compounds is that having the formula

V

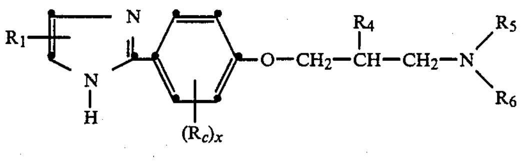

where $R_1$ is selected from —$CH_3$, H, phenyl, pentafluorophenyl, p-chlorophenyl, p-fluorophenyl, p-methoxyphenyl, 2-thienyl, —$CF_3$— and pyridyl; x is 0, 1, 2 or 3 and $R_c$ is halo preferably chloro, $C_1$–$C_3$ alkyl preferably —$CH_3$, and cyano.

Another series of preferred compounds are those having the formula V where $R_4$ is —OH.

In a particularly preferred series of compounds having formula V, $R_4$ is OH and only one of $R_5$ and $R_6$ is $C_1$–$C_6$ alkyl, preferably cyclic or branched $C_3$–$C_4$ alkyl such as tert-butyl, cyclopropyl, 1-methyl-3-phenylpropyl, 1-methyl-2-phenylethyl and the like.

An especially preferred series of compounds is one having formula V where $R_1$ is —$CF_3$, $R_4$ is OH and one of $R_5$ and $R_6$ is hydrogen while the other is $C_1$–$C_6$ alkyl, preferably $C_3$–$C_4$ cyclic or branched hydrocarbon alkyl, especially tert-butyl.

The compounds of the present invention include all the optical isomer forms. In other words, the compounds include mixtures containing the optical isomers such as racemic mixtures, as well as the individual optical isomers.

The compounds of the present invention also include the non-toxic pharmacologically acceptable acid addition and quaternary ammonium salts of the present imidazoles. The acid addition salts are prepared by treating the imidazole with an appropriate amount of a suitable organic or inorganic acid. Examples of useful organic acids are carboxylic acids such as maleic acid, tartaric acid, acetic acid, pamoic acid, oxalic acid, propionic acid, salicyclic acid, succinic acid, citric acid, malic acid, isethionic acid and the like; useful inorganic acids are hydrohalo acids such as HCl, HBr and HI, sulfuric acid, $H_3PO_4$ and the like.

The quaternary salts are characterized by the group

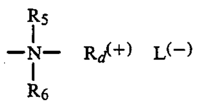

wherein $R_5$ and $R_6$ are $C_1$–$C_6$ alkyl, $R_d$ is $C_1$–$C_6$ alkyl and L is the anion of a non-toxic acid, preferably a halide such as the iodide. These salts are prepared by any suitable method—for example, by reacting any imidazole of the present invention having the tertiary amine group

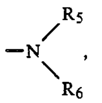

with an alkyl halide, preferably the iodide such as ethyliodide or methyliodide, in a suitable solvent such as methanol, ethanol or dimethylformamide (DMF). The reaction is generally carried out at room temperature. The quaternary salt is obtained directly on removing the solvent.

Compounds of the present invention may be prepared by any convenient method.

One method (Method A) of preparing the present compounds is by amination of a compound having the formula

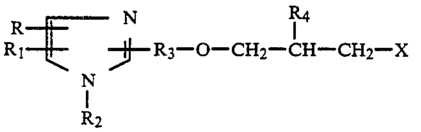

VI where X is a halogen, preferably Br, I or Cl. When $NH_3$ is the aminating agent, X is replaced by $—NH_2$ while when a primary or secondary, acyclic or alicyclic amine is used, X is replaced by the corresponding $—NR_5R_6$ group. Typically, the amination can be carried out by heating a mixture of the halo compound VI and the amine e.g. t-butylamine for a sufficient period of time and then isolating the aminated product. U.S. Pat. No. 3,337,628 disclosed such procedures.

An especially useful method of preparing imidazoles of the present invention wherein $R_4$ is —OH is by reaction of ammonia or a suitable amine reactant with an epoxy compound as illustrated by the following general reaction equation:

METHOD B

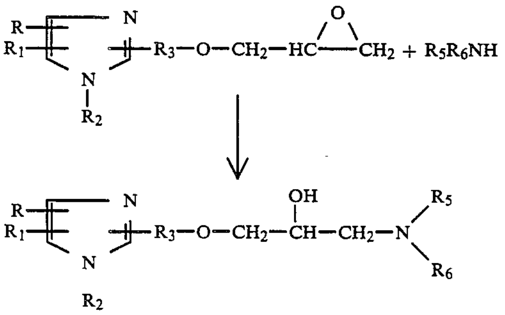

The reaction is generally carried out in solution with excess amine reactant serving as the solvent. However, other solvents may be used such as triethylamine, pyridine, tetrahydrofuran and the like. The reaction is conveniently conducted at reflux temperature. However, the reaction temperature can be varied from room temperature to temperatures above reflux. The reaction may be carried out at atmospheric pressure but it can be carried out at pressures above atmospheric, if desired.

A method of preparing compounds of formula I wherein R and $R_2$ are H, $R_1$ is trihaloalkyl and

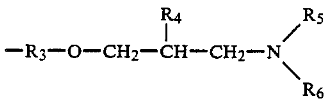

is in the 2 position in the imidazole ring involves the reaction of 1,1,1 trihalo-3,3-dihaloacetone, aryl aldehyde and $NH_3$. Depending on the type aryl aldehyde used, different sequences of reactions are utilized, these are illustrated by the following sets of equations. In these equations X and $X^1$ are halogen selected from F, Br and Cl—and it is preferred that X is F and $X^1$ is Br.

METHOD C

SEQUENCE 1

(1)

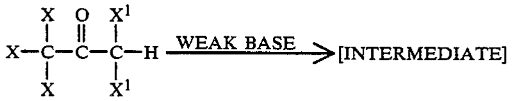

(2) [INTERMEDIATE] +

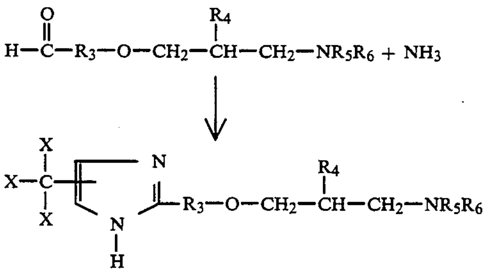

SEQUENCE 2

(1)

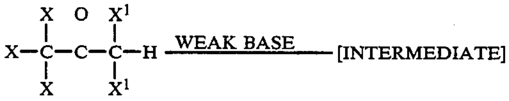

(2) [INTERMEDIATE] +

(3)

(4)

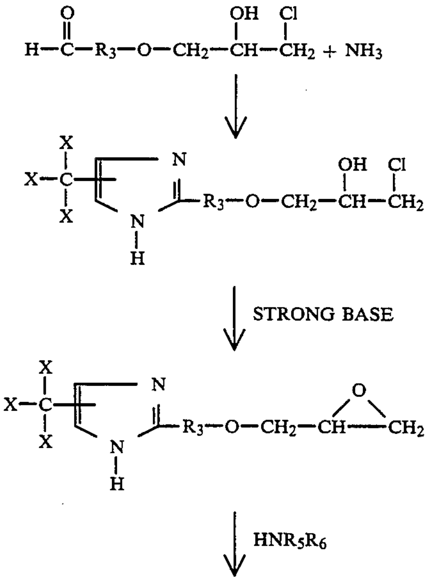

-continued

METHOD C

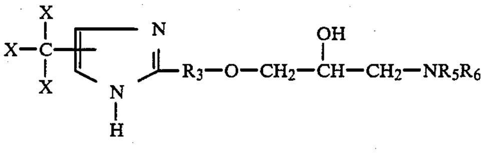

The intermediate in the above equations is believed to be a glyoxal

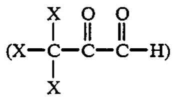

or a hydrated glyoxal

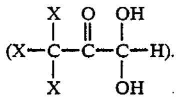

This intermediate is generally prepared as an aqueous mixture by treating the halogenated acetone with a aqueous solution of a weak base such as sodium acetate trihydrate. This solution is heated for a period of time and at a temperature sufficient to form the intermediate. On cooling, the intermediate containing solution is added to a solution of the appropriate arylaldehyde and aqueous ammonia. Any suitable water miscible solvent may be used. Methanol is conveniently used. The reaction to yield the substituted imidazole is generally conducted at room temperature, although elevated temperatures may be used. The solvent is then stripped and the product imidazole is recovered.

Where the imidazole intermediate has the

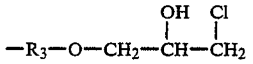

substituent, this intermediate is treated with a suitable strong base such as KOH, potassium butoxide, NaOH, or the like, in a solvent such as methanol, to effect conversion to the epoxy

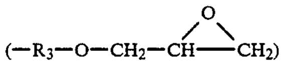

group. This epoxy derivative is then converted to the desired amine final product as illustrated above.

Still another method for preparing compounds of formula I where $R_2$ is H and

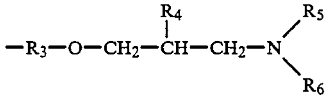

is in the 2 position in the imidazole is by the reaction of aryl aldehyde with a glyoxal or acetal thereof and $NH_3$. When the acetal is used, it must first be hydrolyzed e.g. by treatment with a strong acid solution such as aqueous $H_2SO_4$. This reaction scheme is illustrated by the following equations:

METHOD D

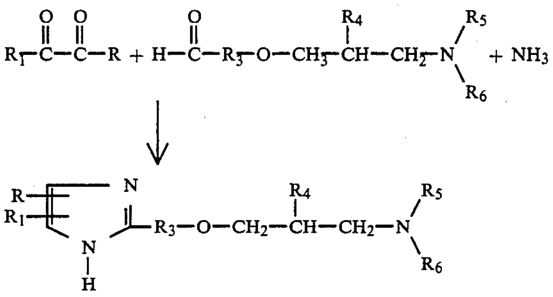

If, in Method D, the aryl aldehyde used has the formula

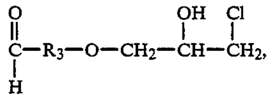

the imidazole product would require dehydrochlorination and treatment with amine, as shown in Method C sequence 2, steps (3) and (4), to afford the imidazole of the present invention.

The process of Method D is generally carried out in solution and at temperatures ranging from about room temperature to about 100° C. Pressure is not required. Solvents used will vary depending on the type of reactants used. Generally, this reaction is carried out in an aqueous solution e.g. $H_2O$ or $H_2O$/miscible alkanol.

Another method for preparing Formula I compounds where $R_2$ is other than H is by treating the corresponding compound where $R_2$ is H with a suitable reagent using a recognized technique.

Where the $R_2$ group is to be an alkyl group, the corresponding Formula I compound where $R_2$ is H is alkylated using a suitable reagent such as diazomethane, an alkyl halide e.g. $C_2H_5$—Br, $C_6H_{13}$—I, n-butylchloride and the like, or a dialkylsulfate.

Where the $R_2$ group is to be an alkenyl group, recognized alkenylating reagents and techniques are used. Illustrative of these techniques is the reaction of the imidazole having $R_2$=H, with NaH followed by treatment with an alkenyl halide e.g. allylbromide to produce the corresponding imidazole having $R_2$=alkenyl.

Where the $R_2$ group is to be hydroxyalkyl, the imidazole wherein $R_2$ is H is reacted with an epoxy compound e.g. 1,2-epoxyethane, 1,2-epoxypropane, 1,2-epoxyhexane to produce the corresponding imidazole where $R_2$ is monohydroxyalkyl. Conditions (temperature, catalysts, solvents etc.) for this type of reaction are disclosed in U.S. Pat. No. 3,786,061 and to the extent necessary the disclosure is incorporated herein by reference.

The aryl aldehyde intermediates having the formula

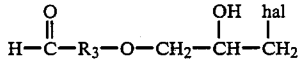

VII where hal is Cl or Br, are conveniently prepared by reacting the corresponding hydroxyaryl aldehyde with epihalohydrin as illustrated by the following reaction equation:

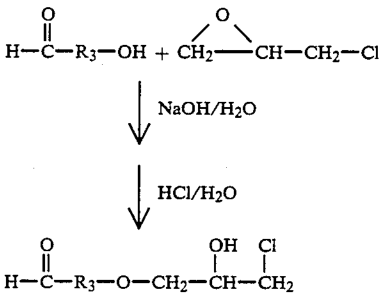

The aryl aldehyde intermediates having formula $O{=}CH{-}R_3{-}O{-}CH_2{-}CHOH{-}CH_2{-}NR_5{-}R_6$ (VIII)

are conveniently prepared by reacting the corresponding hydroxyarylaldehyde with an epihalohydrin as the following equations illustrate:

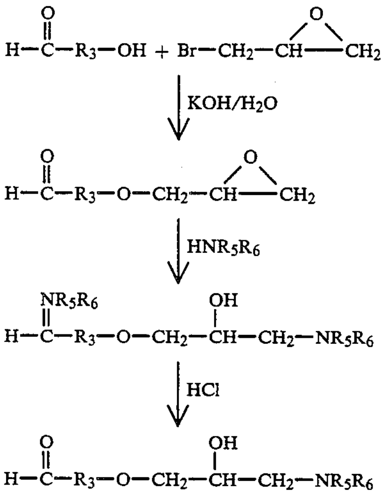

Reaction conditions are similar to those used to prepare the VII compound.

The aryl aldehydes VIII can also be prepared by reacting an aryl aldehyde with an oxazolidine as illustrated by the following equations:

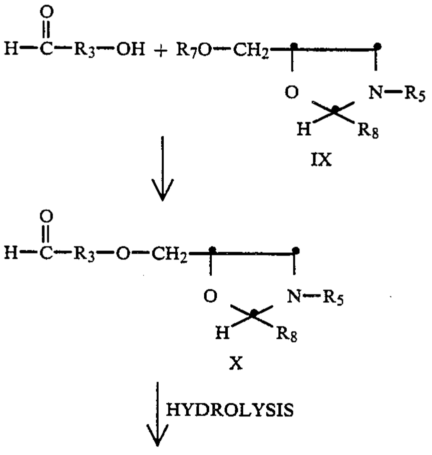

IX

X

-continued

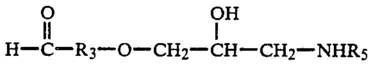

VIIA $R_8$ is the residue of an aldehyde as will be described below. $R_7$ is an alkyl or aryl sulfonyl group e.g. benzene sulfonyl, toluene sulfonyl, methane sulfonyl and the like. This coupling reaction of the oxazolidine IX and the aryl aldehyde is generally carried out in suitable solvent such as dimethylformamide (DMF), dimethylsulfoxide (DMSO), hexamethylenephosphoramide (HMPP), alkanols such as methanol, ethanol and the like. While the reaction can be carried out at temperatures ranging from 0° C. to 200° C., it is conveniently carried out at the reflux temperature of the solution. Conventional techniques and reagents e.g. HCl, $H_2SO_4$, are used to effect the hydrolysis.

The oxazolidine IX is obtained from the reaction of an aldehyde with a 1-amino-2,3-dihydroxypropane followed by treatment with an appropriate alkyl or aryl sulfonyl halide. This reaction is illustrated by the following equations:

(1)

(2)

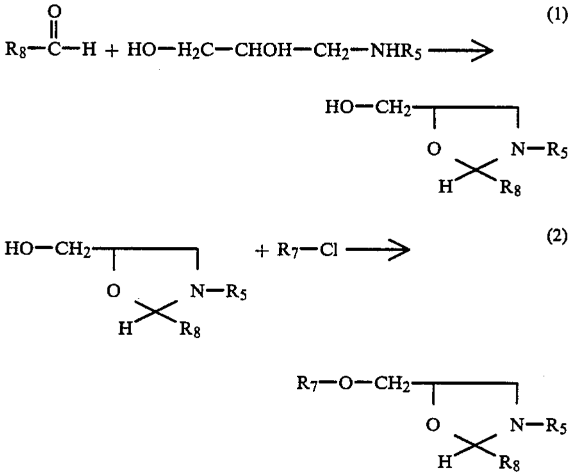

Any

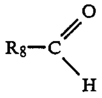

aldehyde may be used provided that it does not adversely affect the oxazolidine preparation. Examples of suitable aldehydes are aryl aldehydes such as benzaldehyde, substituted benzaldehydes, napthylaldehyde, and the like, and alkanals such as acetaldehyde, formaldehyde, butyraldehyde and the like. Commercially available aldehydes are most conveniently used. Processes for preparing oxazolidines are disclosed in U.S. Pat. No. 3,718,647 and U.S. Pat. No. 3,657,237 and to the extent necessary, the pertinent disclosure is incorporated herein by reference.

The imidazoles of the present invention wherein $R_4$ is the ester group

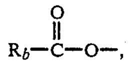

are conveniently prepared by treating the corresponding imidazole wherein $R_4$ is OH with the desired organic acid anhydride or halide, preferably the chloride. This reaction can be carried out at ambient temperature or at elevated temperature up to about 100° C. When $R_2$ in the starting imidazole is hydrogen, then in order to avoid acylating the 1-nitrogen in the imidazole the reaction is carried out under acidic conditions. The general reaction is illustrated by the following equation:

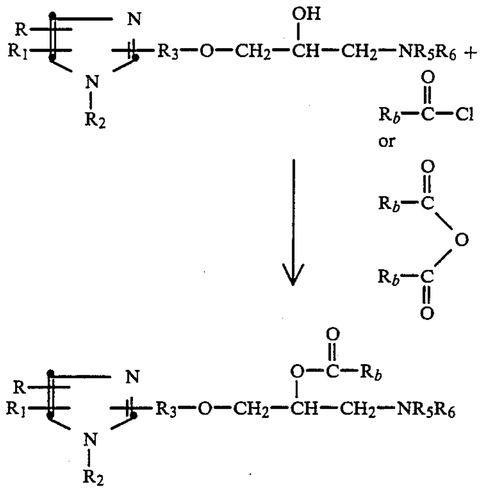

The present imidazoles encompass all optical isomer forms, that is, mixtures of isomers e.g. racemates as well as the individual optical isomers. These individual isomers are commonly designated, according to the optical rotation they effect, by (−) and (+), (L) and (D) or a combination of these signs and letters. These optical isomers may also be designated according to their absolute spatial configuration, by the symbols (S) for sinister and (R) for rectus.

Ordinarily, the imidazoles of the present invention are obtained as racemates. These racemates can be separated into the individual optical isomers using techniques available in the art. These methods are normally tedious, time consuming and rarely effect a complete separation of isomers. This separation of isomers can be circumvented and one or the other optical isomer of the present imidazoles can be directly prepared by utilizing a single enantiomer of the oxazolidine IX to prepare a single optical isomer of the aryl aldeyde intermediate VIII. By using this single isomer intermediate, a single optical isomer form of the desired imidazole final product can be obtained. The single optical isomer of the oxazolidine IX is conveniently obtained by using a single optical isomer of the 1-amino-2,3-dihydroxypropane reactant in the oxazolidine preparation disclosed above.

Compounds of formula I wherein the

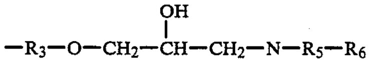

is in the 4-position in the imidazole ring can be prepared according to the method illustrated by the following equations:

METHOD E (1)

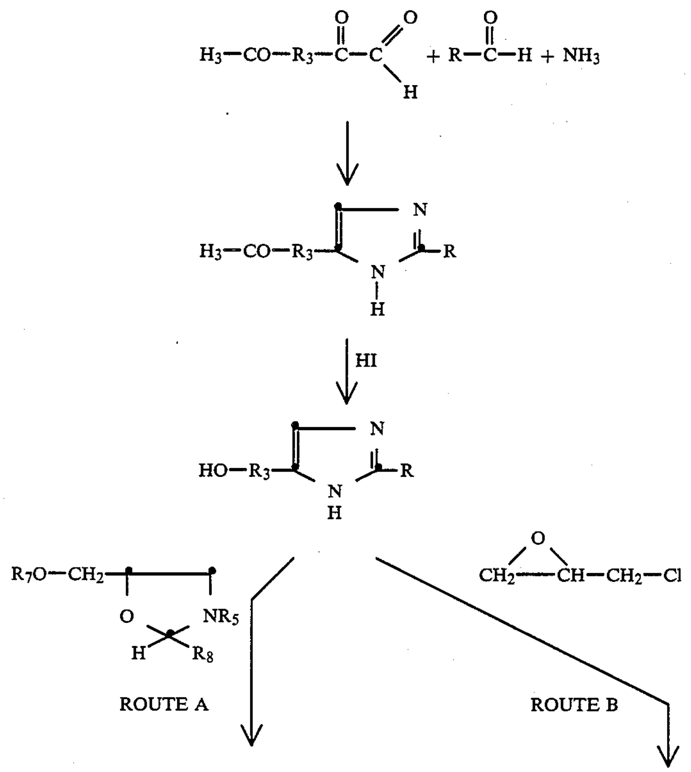

-continued

METHOD E

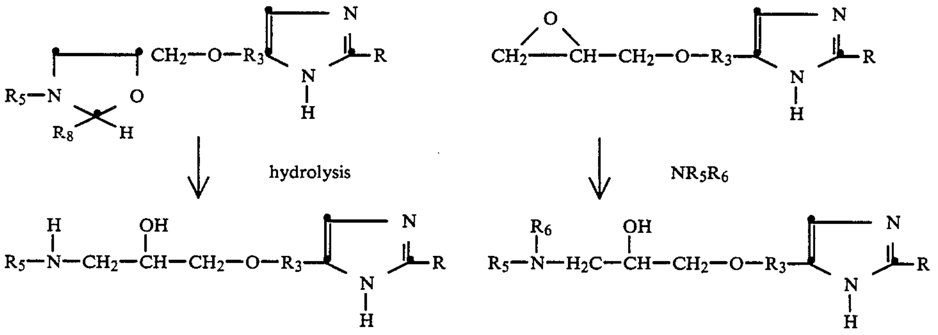

Method E, as the equation illustrated, involves the reaction of alkoxyarylacetal with an aldehyde in the presence of ammonia. This ammonia may be liquid ammonia wherein the reaction temperature would range from about −33° C. up to about 70° C., the reaction being carried out under pressure where the temperature requires. The ammonia may also be provided as aqueous solution i.e. ammonia hydroxide, in which case reaction temperatures of from about the freezing point of the reaction mixture to about 100° C. can be used. With the aqueous ammonia system, room temperature is conveniently used. Other water miscible aqueous solvents such as the lower alkanol e.g. $CH_3OH$, or DMF may also be used as necessary. The ether cleavage, step (2), may be accomplished using any suitable reagents and procedure such as aqueous HI or aqueous HBr; or $AlCl_3$ in a hydrocarbon solvent (hexane, benzene etc.). The Method E route A of course permits preparation of a single optical isomer—while the route B results in a racemate.

The compounds of the present invention are active (1) as antihypertensives, i.e. they have an immediate blood pressure lowering effect in hypertensive animals and (2) as β-adrenergic blocking agents. Many of the present imidazoles also are active vasodilators.

The antihypertensive effect was determined by administering (orally or intraperitoneally) the present compounds to spontaneously hypertensive (SH) rats and measuring the effect on the blood pressure. Representative imidazoles, generally administered as salts e.g. the hydrochloride, were found to lower the SH rat's blood pressure.

The β-adrenergic blocking activity (β-blockade) of the present compounds was determined by measuring the ability of representative compounds to block isoproterenol induced tachychardia, vasodepression and bronchodilatation in animals. Intravenous administration of the imidazole, (generally as an acid addition salt) was used for this evaluation. Representative imidazoles showed ability to effect β-blockade in addition to having the aforesaid antihypertensive effect of immediate onset.

Representative compounds which were tested and found to have antihypertensive and β-adrenergic blocking activity are listed below. The compounds were racemates except where otherwise indicated.

| No. | COMPOUND |
| --- | --- |
| 1 | 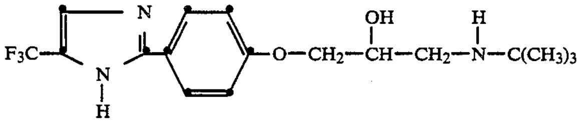 |
| 2 | 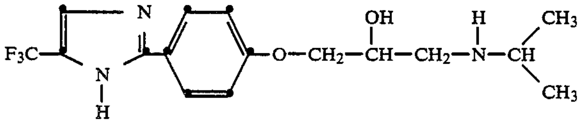 |
| 3 | 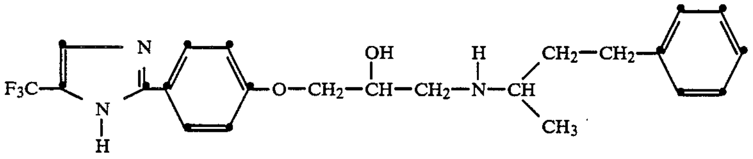 |
| 4 | 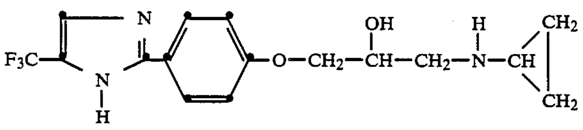 |

-continued
| No. | COMPOUND |
|---|---|
| 5 | 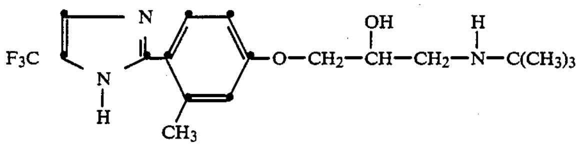 |
| 6 | 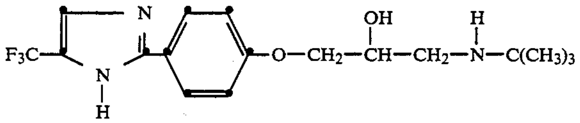 |
| | (S) ISOMER |
| 7 | 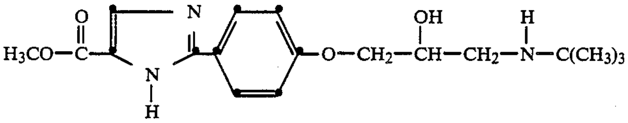 |
| 8 | 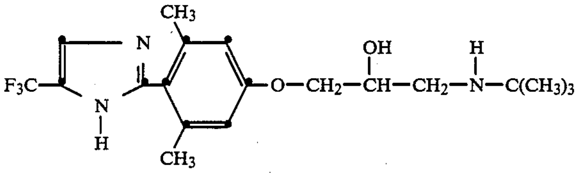 |
| 9 | 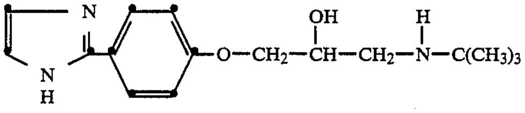 |
| 10 | 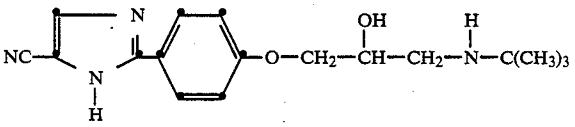 |
| 11 | 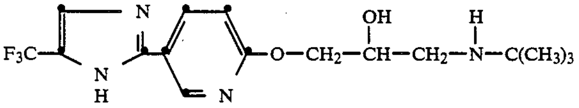 |
| 12 | 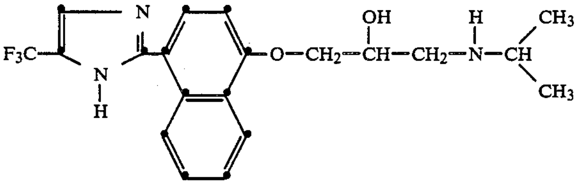 |
| 13 | 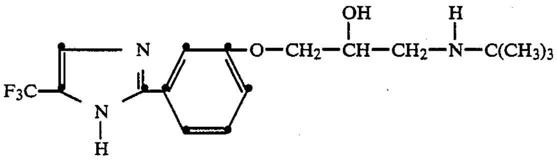 |
| 14 | 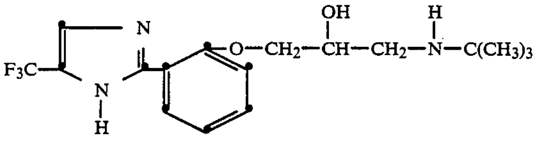 |

-continued

| No. | COMPOUND |
|---|---|
| 15 | 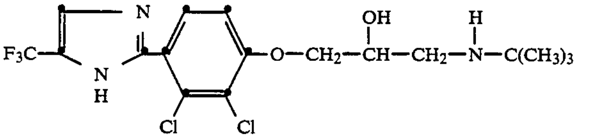 |
| 16 | 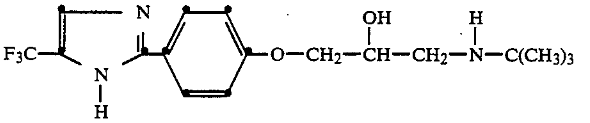 |
| 17 | 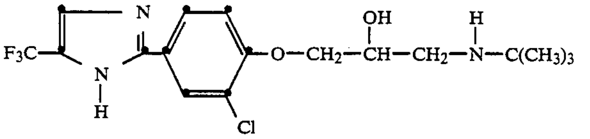 |
| 18 | 2-[4-(3-tert.-butyl-2-hydroxypropoxy)phenyl]-4-(3-pyridyl)imidazole |
| 19 | 1-methyl-2-[4-(3-tert.-butyl-2-hydroxypropoxy)phenyl]-4(and 5)-trifluoromethylimidazole |

In evaluating the $\beta$-blocking effectiveness of the present compounds, it was noted that many of the compounds exhibit some cardioselectivity that is the compound is more effective in reducing the heart rate effects of isoproterenol than it is in blocking the isoproterenol effects on the bronchi. Expressed in different terms, a smaller amount of the compound is required to block isoproterenol-induced elevation in heart rate than is required to block the isoproterenol-induced relaxation of the bronchi. This cardioselectivity factor can be expressed as the ratio of $ED_{50}$ for pulmonary effect ($\beta_2$):$ED_{50}$ for cardiac effect ($\beta_1$). Where the $\beta_2$:$\beta_1$ ratio is over 1, then the compound would be considered to have cardioselective activity. The tested compounds numbered 1-11 above are examples of compounds having $\beta_2$:$\beta_1$ ratios greater than 1.

The ability of the compounds of the present invention to reduce blood pressure in the SH rat indicates that the compounds and their salts may be useful to treat essential hypertension in humans.

The $\beta$-adrenergic blocking effectiveness of the compounds of the present invention indicates that they are also useful to treat humans suffering from undesirable conditions such as angina pectoris or certain arrhythmias which are known to be amenable to treatment with $\beta$-adrenergic blocking agents. Furthermore, the cardioselective nature of some of the present compounds offers the advantage of limiting blockade to only the $\beta_1$ receptors, i.e. those which control heart rate.

For use as antihypertensives and/or $\beta$-adrenergic blocking agents, the present compounds can be administered orally or parenterally i.e. intravenously, inerperitoneally, etc. and in any suitable dosage form. The compounds may be offered in a form (a) for oral administration e.g. as tablets in combination with other compounding ingredients customarily used such as talc, vegetable oils, polyols, benzyl alcohols, gums, gelatine, starches and other carriers; dissolved or dispersed or emulsified in a suitable liquid carrier; in capsules or encapsulated in a suitable encapsulating material or (b) for parenteral administration e.g. dissolved or dispersed in a suitable liquid carrier or emulsified or (c) as an aerosol. The ratio of active compound to compounding ingredients i.e. carrier, diluent etc. will vary as the dosage form requires. Whatever dosage form is used, the amount of compound of the present invention administered should be sufficient to effect (a) a reduction in blood pressure of the patient suffering from hypertension and/or (b) desirable level of $\beta$-blockade in the patient. Generally, doses of the present compounds of from about 0.01 to about 50 mg/kg and preferably from about 0.1 to about 20 mg/kg of body weight per day may be used. Dosage may be single or multiple depending on the daily total required and the unit dosage.

Following are examples illustrating representative pharmaceutical formulations containing imidazoles of the present invention. Conventional techniques are used to prepare these formulations

| INGREDIENT | AMOUNT (Mg.) |
|---|---|
| TABLET FORMULATION I | |
| (S)—2[4-(3-tert-butylamino-2-hydroxypropoxy)phenyl]-4-methylimidazole | 40.0 |
| calcium phosphate | 120.0 |
| lactose | 50.0 |
| starch | 23.5 |
| magnesium stearate | 1.5 |
| TABLET FORMULATION II | |
| 2-[4-(3-cyclopropylamino-2-hydroxypropoxy)phenyl]-4-trifluoromethylimidazole | 80 |
| Starch paste - 12½%, 100 cc allon. | 12.5 |
| | 512.5 |
| Starch, U.S.P. corn | 25.0 |
| Magnesium stearate | 5.5 |
| CAPSULE FORMULATION | |
| (S)—2[4-(3-tert-butylamino-2-hydroxypropoxy)phenyl]-4-p-methoxyphenylimidazole dihydrochloride dihydrage | 250 |
| lactose, U.S.P. | 93 |
| talc | 7 |
| INJECTABLE SOLUTION | |
| 2-[4-(3-isopropylamino-2-hydroxypropoxy)phenyl]-4-cyanoimidazole hydrochloride | 5 |
| sodium chloride | 9 |
| distilled water, q.s. 1.0 ml. | |

-continued

| INGREDIENT | AMOUNT (g/l) |
|---|---|
| LIQUID SUSPENSION | |
| (S)—2-[4-(3-methylamino-2-hydroxy-propoxy)phenyl]-4-(4-pyridyl) imidazole | 5.0 |
| Veegum H.V. | 3.0 |
| methyl parable | 1.0 |
| kaolin | 10.0 |
| glycerin | 250.0 |
| water, q.s. → 1 liter | |

The following examples illustrate preparation of representative imidazoles of the present invention. All parts and percentages are by weight unless otherwise indicated.

EXAMPLE 1

A. Preparation of 3-(3-Chloro-2-hydroxypropoxy)-Benzaldehyde

A mixture of m-hydroxybenzaldehyde (24.4 g.), epichlorohydrin (55.2 g.), and pyridine (0.4 ml.) is heated 5 hours at 100° C. and then concentrated under reduced pressure (20 mm. Hg.) over steam. The residual oil is taken up in chloroform (200 ml.), concentrated hydrochloric acid (50 ml.) is added, and the mixture is stirred 0.5 hours at room temperature. The chloroform layer is separated, washed with water, and the chloroform removed under reduced pressure (20 mm. Hg.) over steam. Distillation of the residual oil yields 28.9 g. of 3-(3-chloro-2-hydroxypropoxy)-benzaldehyde as a yellow-brown oil, b.p. 166° C./0.25 mm. Hg.

B. Preparation of 2-[3-(3-Chloro-2-hydroxypropoxy)phenyl]-4-trifluoromethylimidazole To a solution of sodium acetate trihydrate (11.6 g.) in water (40 ml.) is added trifluorodibromoacetone (11.6 g.) and the resulting solution is heated 0.5 hours at 100° C. After cooling to room temperature, it is added to one portion to a solution of 3-(3-chloro-2-hydroxypropoxy)-benzaldehyde (9.45 g.) in methanol (100 ml.) and aqueous ammonia 50 ml.). The resulting cloudy solution is allowed to stand 5 hours at room temperature and the methanol is removed under reduced pressure (20 mm Hg.) over steam. An oil separates and crystallizes. The supernatant liquid is decanted and the residue is triturated with benzene and isolated by filtration to yield 6.97 g. of solid. After recrystallization from toluene, the solid is suspended in warm water and acetonitrile added to cause solution. Upon cooling, 2-[3-(3-chloro-2-hydroxypropoxy)phenyl]-4-trifluoromethylimidazole is obtained as a white solid, m.p. 181°–183° C.

C. Preparation of 2-[3-(2,3-Epoxypropoxy)phenyl]-4-trifluoromethylimidazole

To a solution of 2-[3-(3-chloro-2-hydroxypropoxy)-phenyl]-4-trifluoromethylimidazole (3.8 g.) in methanol (150 ml.) is added powdered potassium hydroxide (3. g.) and the mixture is allowed to stir 4 hours at room temperature. Glacial acetic acid (2.75 ml.) is added and the mixture concentrated under reduced pressure (20 mm. Hg.) over steam. The resulting residue is stirred with water, filtered and recrystallized from xylene to yield 2.5 g. of 2-[3-(2,3-epoxypropoxy)phenyl]-4-trifluoromethylimidazole is obtained, m.p. 145°–146.5° C.

D. Preparation of 2-[3-(3-Isopropylamino-2-hydroxypropoxy)phenyl]-4-trifluoromethylimidazole A solution of 2-[3-(2,3-epoxypropoxy)phenyl]-4-trifluoromethylimidazole (0.9 g.) in isopropylamine (10 ml.) is heated 6 hours at reflux. The excess isopropylamine is removed by distillation at atmospheric pressure over steam. The residue is triturated with nitromethane (5 ml.) and the resulting solid removed by filtration. After recrystallization from nitromethane 0.65 g. of 2-[3-(3-isopropylamino-2-hydroxypropoxy)phenyl]-4-trifluoromethylimidazole is obtained, m.p. 162.5°–163.5° C.

EXAMPLE 2

Preparation of 2-[4-(3-isopropylamino-2-hydroxypropoxy)phenyl]-4-trifluoromethylimidazole A solution of 2-[4-(2.3-epoxypropoxy)phenyl]-4-trifluoromethylimidazole (1 g) in isopropylamine (10 ml.) is heated 7 hours at reflux and then allowed to stand 16 hours at room temperature. The excess isopropylamine is removed by distillation at atmospheric pressure and the residue is triturated with nitromethane to yield a solid. After filtration and recrystallization from acetonitrile, 0.6 g. of 2-[4-(3-isopropylamino-2-hydroxypropoxy)phenyl]-4-trifluoromethylimidazole is obtained, m.p. 173°–173.5° C.

EXAMPLE 3

A. Preparation of 2-methyl-4-(2,3-epoxypropoxy)benzaldehyde

To epichlorohydrin (20 g., 0.216 mole) heated at 55° C. is added dropwise a solution of 2-methyl-4-hydroxybenzaldehyde (9.0 g., 0.066 mole) in 2.5N sodium hydroxide solution (40 ml.). After the addition, the solution is allowed to stir an additional 3 hours at 55° C. and then at room temperature overnight. The oil is distilled to give 8.3 g. of 2-methyl-4-(2,3-epoxypropyl)benzaldehyde, m.p. 160°–170° C. at 1 mm. Hg.

B. Preparation of 2-methyl-4-(3-tert.-butylamino-2-hydroxypropoxy)benzaldehyde To a methyl-4-(2,3-epoxypropoxy)benzaldehyde (8.3 g., 0.043 mole) is added tert-butylamine (10 g., 0.137 mole) and the resulting solution refluxed for 2 hours and allowed to stand overnight at room temperature. The excess tert butylamine is removed under reduced pressure (20 mm. Hg.), the residue is heated on a steam bath with 6N hydrochloric acid (50 ml.) for 5 hours, and then basified while hot with solid sodium hydroxide. The mixture is cooled to room temperature, extracted with chloroform (3×50 ml.), dried over sodium sulfate, filtered and concentrated to dryness. The residual oil is crystallized from hexane to give 8.75 g. of 2-methyl-4-(3-tert.-butylamino-2-hydroxypropoxy)benzaldehyde, m.p. 82°–84° C.

C. Preparation of 2-[2-methyl-4-(3-tert.-butylamino-2-hydroxypropoxy)-phenyl]-4-trifluoromethylimidazole To sodium acetate trihydrate (6.26 g., 0.046 mole) in water (26 ml.) is added dibromotrifluoroacetone (6.26 g., 0.023 mole). The solution is heated for 45 minutes on a steam bath, cooled, and added to a solution of 2-methyl-4-(3tert.-butylamino-2-hydroxypropoxy)benzaldehyde (3.05 g., 0.0115 mole) in methanol (60 ml.) and concentrated aqueous ammonia (20 ml.). The solution is allowed to stand for 5 hours at room temperature. The methanol is removed under reduced pressure (20 mm. Hg.) over steam and the residue treated with chloroform (3×50 ml.) and saturated sodium carbonate (50 ml.). The organic layer is concentrated to dryness and the residue crystallized from acetonitrile to give 1.2 g. of 2-[2-methyl-4-(3-tert.-butylamino-2-hydroxypropoxy)phenyl]-4-trifluoromethylimidazole, m.p. 162°–164° C.

EXAMPLE 4

Preparation of 2-[4-(3-tert. butylamino-2-hydroxypropoxy)phenyl]-4-phenylimidazole A solution of p-(3-tert. butylamino-2-hydroxypropoxy)benzaldehyde (5.0 g., 0.02 mole), phenylglyoxal monohydrate (6.04 g., 0.04 mole), concentrated aqueous ammonia (50 ml.), water (50 ml.) and methanol (200 ml.) is allowed to stand at room temperature for 5 hours. The solution is concentrated to a residual oil under reduced pressure (20 mm. Hg.) and treated with saturated sodium carbonate (50 ml.) and chloroform (3×50 ml.). The organic layer is concentrated to dryness and chromatographed on neutral alumina (500 g.) using a gradient elution technique starting with chloroform. The product is eluted with 10% methanol-90% chloroform. Final purification is accomplished by passing through a column of silica gel (150 g.) and eluted with 20% methanol-80% chloroform. The solvent is removed under reduced pressure (20 mm. Hg.) and the residue crystallized from acetonitrile to give 0.7 g. of 2-[4-(3-tert. butylamino-2-hydroxypropoxy)-phenyl]-4-phenylimidazole, m.p. 176°–178° C.

S-4-[3-(3,4-dimethoxyphenylethyl)amino-2-hydroxypropoxy]benzaldehyde is used in place of p-(3-tert. butylamino-2-hydroxypropyl)benzaldehyde and 2-thienylglyoxal is used in place of phenyl glyoxal monohydrate in Example 4 to obtain S-2-[4-(3,4-dimethoxyphenylethylamino)-2-hydroxypropoxy]phenyl-4-(2-thienyl)imidazole.

EXAMPLE 5

A. Preparation of S-4-(3-tert. butylamino-2-hydroxypropoxy)benzaldehyde

To a solution of S-2-phenyl-3-tert. butyl-5-hydroxymethyloxazoldine (47 g., 0.2 mole) in pyridine (75 ml.) is added portionwise p-toluenesulfonyl chloride keeping the internal temperature between 25° and 30° C. The mixture is stirred 2 hours after addition is complete keeping the temperature between 25° and 30° C. Ice water (150 ml.) and potassium carbonate (27.6 g.) are added and the mixture is extracted with chloroform (3×100 ml.). The organic extract is dried over sodium sulfate and concentrated first at 20 mm. Hg. and then at 1 mm. Hg. keeping the temperature below 50° C. The residual oil is dissolved in N,N-dimethylformamide (150 ml.) and added dropwise to a refluxing solution of the sodium salt of p-hydroxybenzaldehyde (0.2 mole) in N,N-dimethylformamide (200 ml.). After refluxing 10 hours, the reaction mixture is concentrated first at 20 mm. Hg. and then at 1 mm. Hg. The residue is treated with 5% sodium hydroxide solution and extracted with chloroform (3×100 ml.). The organic extract is dried over sodium sulfate and the residue chromatographed on alumina (500 g. activity grade II). The chromatographic fractions are concentrated and the residue distilled at 240° C. at 0.3 mm. Hg. The distillate (21 g.) is treated with 1N hydrochloric acid (75 ml.), heated ½ hour over steam, cooled and extracted with ether. The aqueous layer is made basic to pH 10 by the addition of 2% sodium hydroxide solution and extracted with chloroform (3×100 ml.). The organic extract is dried over sodium sulfate and concentrated to an oil which after crystallization from hexane yields 14.5 g. of S-4-(3-tert. butylamino-2-hydroxypropoxy)benzaldehyde, m.p. 60°–62° C.

(S)-2-phenyl-3-(3,4-dimethoxyphenylethyl)-5-hydroxymethyloxazolidine is used in place of (S)-2-phenyl-3-tert. butyl-5-hydroxymethyloxazolidine in the A. process to yield (S)-4-[3-(3,4-dimethoxyphenylethyl-)amino-2-hydroxypropoxy]benzaldehyde.

B. Preparation of S-2-[4-(3-tert. butylamino-2-hydroxypropoxy)phenyl]-4-trifluoromethylimidazole To sodium acetate trihydrate (20.2 g., 0.15 mole) in water (100 ml.) is added dibromotrifluoroacetone (20.2 g., 0.075 mole). The solution is heated 45 minutes on a steam bath, cooled and is added to a solution of S-p-(3-tert. butylamino-2-hydroxypropoxy)benzaldehyde (12.5 g., 0.05 mole) in methanol (200 ml.) and concentrated aqueous ammonia (75 ml.). The solution is allowed to stand 5 hours at room temperature. The methanol is removed by distillation under reduced pressure (20 mm. Hg.) over steam. The mixture is made basic with saturated aqueous sodium carbonate solution and extracted with ethyl acetate (3×100 ml.). The organic extract is dried over sodium sulfate and concentrated at 20 mm. Hg. over steam. The resulting residue is recrystallized from acetonitrile to yield 7.6 g. of S-2-[4-(3-tert. butylamino-2-hydroxypropoxy)phenyl]-4-trifluoromethylimidazole, m.p. 181°–182° C.

Other Formula I imidazoles prepared using the procedures substantially as described in Examples 1–5 are listed in the following table. It is to be understood that analogous reactants are used to obtain the particular imidazole products.

TABLE 1
PREPARED IMIDAZOLES OF FORMULA
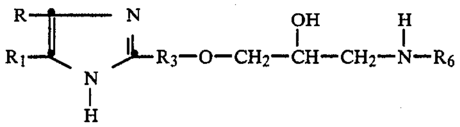
| Example No. | Using Procedure of Example | Imidazole Substitiuents R | R1 | R3 | R6 | M.P. (°C.) |
|---|---|---|---|---|---|---|
| 6 | 1 | H | —$CF_3$ | 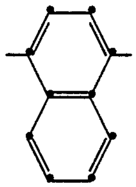 | t-butyl | 207°-210° |
| 7 | 2 | H | —$CF_3$ | 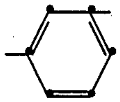 | t-butyl | 139°-141° |
| 8 | 2 | H | —$CF_3$ | 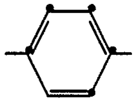 | 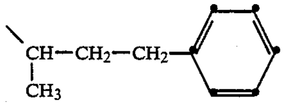 | 159°-170° |
| 10 | 2 | H | —$CF_3$ | 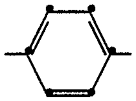 | n-propyl | 153°-155° |
| 9 | 2 | H | —$CF_3$ | 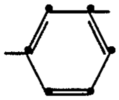 | 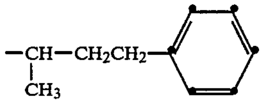 | 120°-133 |
| 11 | 2 | H | —$CF_3$ | 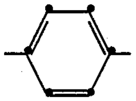 | cyclo-propyl | 163.5°-165° |
| 12 | 3 | H | —$CF_3$ | 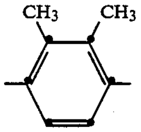 | t-butyl | 187°-190° |
| 13 | 3 | H | —$CF_3$ | 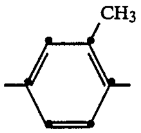 | t-butyl | 183°-185° |
| 13a | 3 | H | —$CF_3$ | 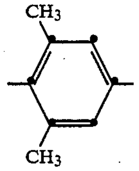 | t-butyl | 159°162° |

TABLE 1-continued
PREPARED IMIDAZOLES OF FORMULA
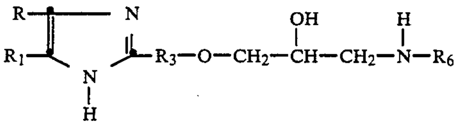
| Example No. | Using Procedure of Example | Imidazole Substitiuents R | R1 | R3 | R6 | M.P. (°C.) |
|---|---|---|---|---|---|---|
| 14 | 3 | H | $-CF_3$ | 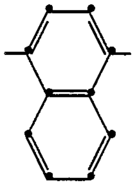 | isopropyl | 210°-213° |
| 15 | 3 | H | $-CF_3$ | 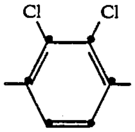 | t-butyl | 181°-182° |
| 16 | 3 | H | $-CF_3$ | 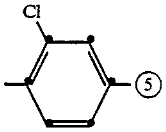 (5) | t-butyl | 167°-171° |
| 17 | 3 | H | $-CF_3$ | 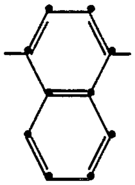 | t-butyl | 207°-210° |
| 18 | 3 | H | $-CF_3$ | 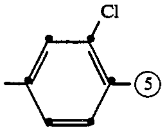 (5) | t-butyl | 174°-177° |
| 19 (1) | 4 | 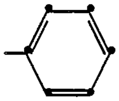 | 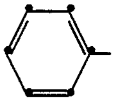 | 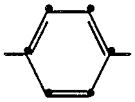 | t-butyl | 180°-181° |
| 20 | 4 | H | H | 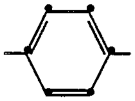 | t-butyl | 162°-164° |
| 21 | 4 | H | H | 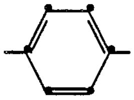 | t-butyl | 193.5°-196° (2) |
| 22 | 4 | H | 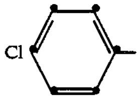 | 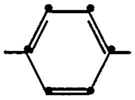 | t-butyl | 186°-188° |

TABLE 1-continued
PREPARED IMIDAZOLES OF FORMULA
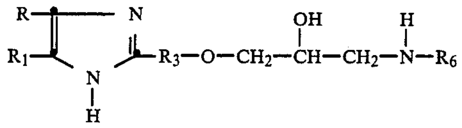
| Example No. | Using Procedure of Example | R | $R_1$ | $R_3$ | $R_6$ | M.P. (°C.) |
|---|---|---|---|---|---|---|
| | | Imidazole Substitiuents | | | | |
| 23 | 4 | H | 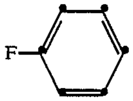 | 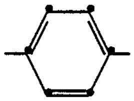 | t-butyl | 167°-169° |
| 24 | 4 | H | 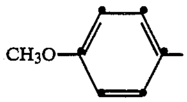 | 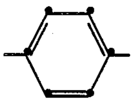 | t-butyl | 179°-181° |
| 25 | 4 | H | 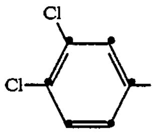 | 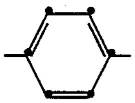 | t-butyl | 189°-190° |
| 26 | 4 | H | 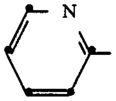 | 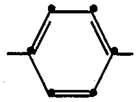 | t-butyl | 101°-105° |
| 27 | 4 | H | H | 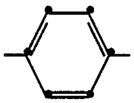 | t-butyl | 158°-162° (3) |
| 28 | 4 | H | 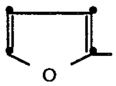 | 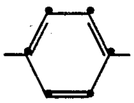 | t-butyl | 172°-173° |
| 29 | 4 | H | 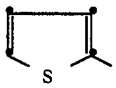 | 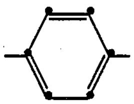 | t-butyl | 178°-180° |
| 30 | 4 | H | 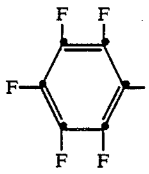 | 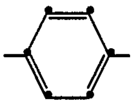 | t-butyl | 168°-170° |
| 31 | 5 | H | $-CF_3$ | 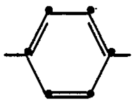 | t-butyl | 178°-179.5° (4) |
| 32 | 5 | H | $-CF_3$ | 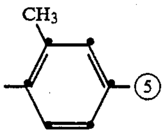 (5) | t-butyl | 141°-143° (3) |

TABLE 1-continued

PREPARED IMIDAZOLES OF FORMULA

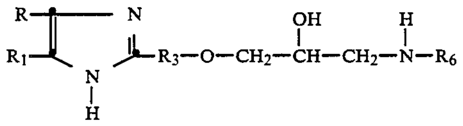

| Example No. | Using Procedure of Example | Imidazole Substitiuents R | $R_1$ | $R_3$ | $R_6$ | M.P. (°C.) |
|---|---|---|---|---|---|---|
| 33 | 5 | H | $-CF_3$ | 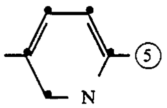 | t-butyl | 110°–120° |

(1) The glyoxal reagent used was 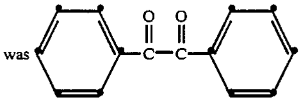

(2) HCl Salt
(3) S—isomer
(4) R—isomer
(5) $O{-}CH_2{-}\overset{OH}{CH_2}{-}CH_2{-}\overset{H}{N}R_6$ attached at this position
(6) Monohydrate: S—Isomer Additional Examples illustrating preparation of other imidazoles of the present invention follow. All parts and percentages are by weight unless otherwise indicated.

EXAMPLE 34

A. Preparation of 2-[4-(3-Chloro-2-hydroxypropoxy)phenyl]-4-trifluoromethylimidazole To sodium acetate trihydrate (5.8 g.) in water (20 ml.) is added trifluorodibromoacetone (5.8 g.); the resulting mixture is heated 0.5 hours on a steam bath. After cooling, the solution is added to p-(3-chloro-2-hydroxypropoxy)benzaldehyde (4.2 g.) in methanol (100 ml.) and concentrated aqueous ammonia (25 ml.). After standing 4.5 hours at room temperature, the methanol is removed by distillation at 20 mm. Hg. over steam; a solid separates and is filtered. After recrystallization from nitromethane, 1.65 g. of 2-[4-(3-chloro-2-hydroxypropoxy)phenyl]-4-trifluoromethylimidazole is obtained, m.p. 181°–183° C.

B. Preparation of 2-[4-(2,3-Epoxypropoxy)phenyl]-4-trifluoromethylimidazole

To a solution of 2-[p-(3-chloro-2-hydroxypropoxy)-phenyl]-4-trifluoromethylimidazole (1.92 g.) in methanol (100 ml.) is added crushed potassium hydroxide (1.5 g.). The mixture is stirred 3 hours at room temperature, neutralized with acetic acid and concentrated under reduced pressure (20 mm. Hg.) over steam. The residue is triturated with water (25 ml.), filtered and recrystallized by dissolving in benzene and adding hexane until turbid. A yield of 1.2 g. of 2-[4-(2,3-epoxypropoxy)-phenyl]-4-trifluoromethylimidazole is obtained, m.p. 152°–153.5° C.

C. Preparation of 2-[4-(3-tert. Butylamino-2-hydroxypropoxy)phenyl]-4-trifluoromethylimidazole A solution of 2-[4-(2,3-epoxypropoxy)phenyl]trifluoromethylimidazole (2.5 g.) in tert. butylamine (20 ml.) is heated 6 hours at reflux. The excess tert. butylamine is removed by distillation at atmospheric pressure over steam. The residue is triturated with nitromethane (5 ml.) and the resulting solid removed by filtration. After recrystallization from acetonitrile, (1.2 g.) of 2-[4-(3-tert. butylamino-2-hydroxypropoxy)phenyl]-4-trifluoromethylimidazole is obtained, m.p. 185.5°–186.5° C.

EXAMPLE 35

A. Preparation of 4-(3-tert. Butylamino-2-hydroxypropoxy)benzaldehyde

To 4-(2,3-epoxypropoxy)benzaldehyde (20 g.) is added tert. butylamine (50 ml.) and the resulting solution is refluxed 17 hours. The excess tert. butylamine is removed by heating at atmospheric pressure to yield a solid residue. To this residue is added 6N hydrochloric acid (200 ml.) and the resulting mixture is heated 5 hours on a steam bath. The solution is cooled and concentrated to 100 ml. on a steam bath under reduced pressure (20 mm. Hg.). The concentrated solution is made basic to pH 10 with saturated aqueous sodium carbonate and extracted with chloroform. The chloroform extract is concentrated to a solid which after recrystallization from acetonitrile yields 18 g. of 4-(3-tert-.butylamino-2-hydroxypropoxy)benzaldehyde, m.p. 123°–125.5° C.

B. Preparation of 2-[4-(3-tert.Butylamino-2-hydroxypropoxy)phenyl]-4-trifluoromethylimidazole To sodium acetate trihydrate (11.8 g., 0.088 moles) in water (40 ml.) is added dibromotrifluoroacetone (11.8 g., 0.044 moles). The solution is heated 45 minutes on a steam bath, cooled and added to a solution of 4-(3-tert. butylamino-2-hydroxypropoxy)benazldehyde (5 g., 0.02 moles) in methanol (200 ml.) and concentrated aqueous ammonia (25 ml.). The solution is allowed to stand 5 hours at room temperature. The methanol is removed under reduced pressure (20 mm. Hg.) over steam and chloroform (50 ml.) and saturated aqueous sodium carbonate (25 ml.) are added to the residue. After stirring a solid separates is filtered and washed with water. After recrystallization from acetonitrile, 3 g. of 2-[4-(3-tert-.butylamino-2-hydroxypropoxy)phenyl]-4-trifluoromethylimidazole is obtained, m.p. 189°-191° C.

EXAMPLE 36

A. Preparation of Salicylaldehyde Diethyl acetal

A mixture of salicylaldehyde (80 g., 0.0655 mole), triethylorthoformate (110 g., 0.765 mole), absolute ethanol (40 ml.) and concentrated sulfuric acid (3 drops) is heated to reflux overnight. The volatiles are removed under reduced pressure (20 mm. Hg.) over steam to give diethyl acetal of salicylaldehyde which is used without further purification.

B. Preparation of 2-(2,3-Epoxypropoxy)benzaldehyde Diethyl acetal

To epichlorohydrin (37 g., 0.4 mole) heated at 50° C. is added dropwise a solution of salicylaldehyde diethyl acetal (25 g., 0.13 mole) in 2N sodium hydroxide solution (200 ml.) and the mixture allowed to stir overnight at 50° C. The reaction mixture is extracted with chloroform (3×100 ml.), dried over potassium carbonate, and concentrated to dryness to give 34.3 g. of 2-(2,3-epoxypropoxy)benzaldehyde diethyl acetal.

C. Preparation of 2-(3-tert. butylamino-2-hydroxypropoxy)benzaldehyde

A solution of 2-(2,3-epoxypropoxy)benzaldehyde diethyl acetal (53 g., 2.1 mole) and tert. butylamine (100 ml.) is heated to reflux for 2 hours and allowed to stand at room temperature overnight. The excess tert. butylamine is removed under reduced pressure (20 mm. Hg.) and the residue heated on a steam bath with 6N hydrochloric acid (300 ml.). After cooling, the solution is neutralized with solid sodium bicarbonate, extracted with chloroform (3×100 ml.), dried over sodium sulfate, filtered and concentrated to dryness. The residue is chromatographed on silica gel (500 ml.) using gradient elution techniques starting with chloroform and the product is obtained with 10% methanol 90% chloroform. After removal of the solvent under reduced pressure (20 mm. Hg.), the residue is crystallized from acetonitrile to give 13.8 g. of 2-(3-tert. butylamino-2-hydroxypropoxy)benzaldehyde, m.p. 156°-160° C.

D. Preparation of 2-[2-(3-tert. butylamino-2-hydroxypropoxy)phenyl]-4-trifluoromethylimidazole To sodium acetate trihydrate (5.4 g., 0.036 mole) in water (20 ml.) is added dibromotrifluoroacetone (5.4 g., 0.02 mole). The solution is heated for 45 minutes on a steam bath, cooled and added to a solution of 2-(3-tert. butylamino-2-hydroxypropoxy)benzaldehyde (3.6 g., 0.0143 mole) in methanol (100 ml.) and concentrated aqueous ammonia (25 ml.). The solution is allowed to stand overnight at room temperature. The methanol is removed by distillation under reduced pressure (20 mm. Hg.) and the residue treated with saturated sodium carbonate (50 ml.), extracted with chloroform (3×50 ml.) and separated. The organic layer is dried over sodium sulfate, filtered and concentrated to dryness. The residue is chromatographed on silica gel (400 ml.) and the product eluted with 20% methanol-80% chloroform. Recrystallization of the product from nitromethane gives 700 mg. of 2-[2-(3-tert. butylamino-2-hydroxypropoxy)phenyl]-4-trifluoromethylimidazole, m.p. 105°-107° C.

EXAMPLE 37

2-[4-(-3-tert. butylamino-2-hydroxypropoxy)phenyl]-4-methylimidazole

To a mixture of cupric acetate (5.0 g., 0.025 mole), acetoxyacetone (1.5 g., 0.013 mole), concentrated aqueous ammonia (25 ml.) is added a solution of p-(3-tert. butylamino-2-hydroxypropoxy)benzaldehyde (3.2 g., 0.0127 mole) in methanol (25 ml.). After the addition, the mixture is heated at reflux overnight. The methanol is removed by distillation under reduced pressure (20 mm. Hg.) over steam and water (200 ml.) is added to the residue. The resulting solution is treated with hydrogen sulfide, filtered through a filter aid, treated with solid potassium carbonate until basic and extracted with chloroform (3×50 ml.). The chloroform is concentrated to dryness and the residue chromatographed on neutral alumina (170 g.) using a gradient elution technique starting with chloroform. The material is eluted off the column using 5% methanol-95% chloroform. The organic solvent is removed by distillation under reduced pressure (20 mm. Hg.) and the residue crystallized from acetonitrile to give 0.79 g. of 2-[4-(3-tert. butylamino-2-hydroxypropoxy)phenyl]-4-methylimidazole, m.p. 202°-203° C.

EXAMPLE 38

A. β-Pyridylglyoxal-dimethylacetal

To a solution of butyl lithium (129 ml., 193N, 0.25 m.) in ether (300 ml.) cooled below −50° C. is added 3-bromopyridine (33.02, 0.209 m.) in ether (60 ml.). The yellow suspension which results is allowed to stir an additional ½ hour at −50° C. and dimethoxyacetic acid piperidide (33.6 g., 0.179 m.) in ether (90 ml.) is added over 1 hour at −50° C. After complete addition, the reaction mixture is allowed to warm to room temperature and heated to reflux for ½ hour. After cooling, a solution of ammonium chloride (500 ml.) is added separated and the aqueous layer extracted with 2×100 ml. ether. The ether layer is washed with 3N $H_2SO_4$, acid; the aqueous layer is neutralized with KOH and extracted with 3×100 ml. $CH_2Cl_2$, dried over $Na_2SO_4$, filtered and concentrated to dryness. The remainder is distilled at 95-100/0.4 mm. to give 13.8 g. of β-pyridylglyoxaldimethylacetal.

B.

4-(3-Pyridyl)-2-[4-(3-tert-butylamino-2-hydroxypropoxy)phenyl]-imidazole

To concentrated sulfuric acid (15 g.) cooled to 0°-4° is added β-pyridylglyoxal-dimethylacetal (5.4 g., 0.03 m) and the solution allowed to stand at room temperature. After 3 days, the mixture is cooled and neutralized with $NaHCO_3$ (26 g., 0.30 m).

To this solution is added water (25 ml.), 37% aqueous ammonia (75 ml.), methanol (25 ml.) and a solution of p-(3-tert-butylamino-2-hydroxypropoxy)benzaldehyde (5.1 g., 0.02 m) in methanol (200 ml.). After standing at room temperature for 3 days, the methanol is removed under reduced pressure (20 mm) over steam, the residue covered with saturated $Na_2CO_3$ (100 ml.), extracted with $CHCl_3$ (3×150 ml.), dried over $Na_2SO_4$, filtered and concentrated to dryness. The residue is chromatographed on silica gel (600 ml.) and the product eluted with 50% $CHCl_3$/MeOH. The crude product is further purified by chromatography on No. 2 neutral alumina (90 g.) and eluted with 2% MeOH/$CHCl_3$. Recrystallization from acetonitrile/chloroform gave 125 mg. of 4-(3-pyridyl)-[4-(3-tert-butylamino-2-hydroxypropoxy)-phenyl]-imidazole.

EXAMPLE 39

(S) Methyl-2-[4-(3-tert-butylamino-2-hydroxypropoxy)-phenyl]imidazole-4-carboxylate To 1N sodium hydroxide solution (20 ml.) is added (S)-2-[4-(3-tert-butylamino-2-hydroxypropoxy)phenyl]-4-trifluoromethylimidazole (1 g.) and the mixture is heated 0.5 hour over steam. The resulting solution is neutralized to pH 7 with concentrated hydrochloric acid and concentrated on a steam bath over a stream of nitrogen. The resulting solid ① is suspended in methanol (25 ml.) saturated with hydrogen chloride. The mixture is refluxed three hours with hydrogen chloride being added after the first and second hour. After being concentrated under reduced pressure (20 mm.) over steam, saturated aqueous solid carbonate solution is added (25 ml.) and the mixture extracted with ethyl acetate. The organic extract was concentrated to a gum which on trituration with aqueous sodium carbonate solidifies and is filtered. After recrystallization from acetonitrile 200 mg. of (S)-methyl 2-[4-(3-tert. butylamino-2-hydroxypropoxy)phenyl]imidazole-4-carboxylate melting at 159°-161° C. is obtained.

① Crude S-2-[4-(3-tert.-butylamino-2-hydroxypropoxy)phenyl]-4-carboxy-imidazole.

EXAMPLE 40

A. S-2-Phenyl-3-Tert. butyl-5-(3-cyano-6-pyridyloxymethyl)oxazolidine

To a solution of S-2-phenyl-3-tert. butyl-5-hydroxymethyloxazolidine (12.35 g., 0.0526 mole) in dimethylformamide (65 ml.) is added sodium hydride (2.22 g., 0.0526 mole of 57%. After heating 25 minutes on a steam bath, the mixture is stirred and cooled to room temperature in 30 minutes and added to a solution of 6-chloronicotinonitrile (7.28 g., 0.0526 mole) in dimethylformamide (35 ml.). The reaction mixture is stirred at room temperature for 4½ hours and then is concentrated under reduced pressure. The fluid residue is taken up in ether and washed with water. The ether solution is dried and concentrated under reduced pressure to yield 18.5 g. of S-2-phenyl-3-tert. butyl-5-(3-cyano-6-pyridyloxymethyl)oxazolidine as an oil.

B. S-6-(3-Tert.butylamino-2-hydroxypropoxy)nicotinonitrile

A suspension of S-2-phenyl-3-tert. butyl-5-(3-cyano-6-pyridyloxymethyl) oxazolidine (18.5 g.) in 1N hydrochloric acid (60 ml.) is heated 5 minutes on a steam bath and then stirred at room temperature for ½ hour. The mixture is extracted with chloroform and the aqueous layer is made basic with 40% sodium hydroxide solution. The basic solution is extracted with ethyl acetate and the extract is dried and concentrated under reduced pressure. The residual white solid is recrystallized from hexane-n-butyl chloride to yield 5.14 g. of S-6-(3-tert. butylamino-2-hydroxypropoxy)nicotinonitrile, m.p. 103°-105° C.

C. S-6-(3-Tert. butylamino-2-hydroxypropoxy)nicotinaldehyde

A suspension of S-6-(3-tert. butylamino-2-hydroxypropoxy)nicotinonitrile (5.14 g. 0.0204 mole) in toluene (128 ml.) in a flamed flask is heated with stirring until a solution is obtained. The toluene is allowed to distill until a total of 21 ml. is collected. Heating is discontinued and the reaction solution is cooled in a dry ice-acetone bath causing the starting material to reprecipitate. To the cold reaction mixture is added diisobutylaluminum hydride in toluene (62.6 ml. 0.075 mole of 0.17 g./ml.) dropwise under nitrogen with stirring. The yellow reaction mixture is stirred cold for 1 hour, and then the acetone bath is removed as methanol (22 drops) is added followed by the addition of water (22 drops). Chloroform is added to the mixture and then water (43 ml.), and after good stirring the mixture is filtered. The filtrate is shaken in a separatory funnel and the organic layer is separated, dried, and concentrated under reduced pressure. To the residual oil is added 1% hydrochloric acid (43 ml.) and the mixture is heated on a steam bath for ½ hour. At this point the pH is basic. Concentrated hydrochloric acid is added until the pH is acid and heating is continued for 15 minutes. The mixture is cooled and made basic with 40% sodium hydroxide solution and then extracted with chloroform. The extract is dried and concentrated under reduced pressure to yield 5.1 g. of S-6-(3-tert. butylamino-2-hydroxypropoxy)nicotinaldehyde as an oil which solidifies.

D. S-2-[2-(3-tert.-Butylamino-2-hydroxypropoxy)-5-pyridyl]-4-trifluoromethylimidazole To sodium acetate trihydrate (2.16 g., 0.016 moles) in $H_2O$ (15 ml.) is added dibromotrifluoroacetone (2.16 g., 0.008 moles) and the mixture is heated ½ hour on a steam bath. After cooling the solution is added to 6-(3-tert.-butylamino-2-hydroxypropoxy)nicotinaldehyde (1 g.) in methanol (50 ml.) and concentrated aqueous ammonium hydroxide (15 ml.). After standing 20 hours at room temperature, the methanol is removed under reduced pressure (20 mm.) over steam. Concentration aqueous sodium carbonate (10 ml.) and ethyl acetate (50 ml.) are added to the concentrated solution. After extracting the organic layer is separated dried over sodium sulfate and concentrated to a gum which is chromatographed on activity grade II alumina with chloroform methanol using a gradient elution technique. The fractions containing product are combined and concentrated to a gum which is dissolved in ethyl acetate. The ethyl acetate solution is washed with saturated sodium carbonate solution, dried and concentrated to yield 2-[2-(3-tert.-butylamino-2-hydroxypropoxy)-5-pyridyl]-4-trifluoromethylimidazole as a non-crystalline solid (650 mg).

This non-crystalline solid was covered with hexane and allowed to stand at about 0° C. for 7 days. The hexane was then decanted and the residue triturated with ether to yield a solid. The ether filtrate also yielded solid on standing at room temperature. These solids were combined and dissolved in benzene. Hexane was added to the point of turbidity, which on cooling yielded a solid. The solid was dried at 66°-73° C. and 0.2 mm for about 48 hours. The dried solid was S-2-[2-(3-tert. butylamino-2-hydroxypropoxy)-5-pyridyl]-4-trifluoromethylimidazole monohydrate (NMR and Mass Spectroscopic analysis), melting at 110°-120° C.

EXAMPLE 41

A. 4-(p-methoxyphenyl)-2-(3-pyridyl)imidazole

A solution of sodium acetate trihydrate (5.8 g, 0.04 m), 3-pyridinecarboxaldehyde (2.3 g., 0.02 m), p-methoxyphenylglyoxal monohydrate (3.92 g., 0.02 m), water (20 ml.), concentrated aqueous ammonia (25 ml.), and methanol (75 ml.) is allowed to stand at room temperature overnight. The solution is concentrated to dryness under reduced pressure (20 mm) over steam, treated with saturated $Na_2CO_3$ (100 ml.) and extracted with chloroform (3×100 ml.). The organic layer is dried over $Na_2SO_4$, filtered and concentrated to dryness. The residue is chromatographed on silica gel (300 ml.) and the product eluted with 3-5% MeOH/$CHCl_3$. The material is crystallized from acetonitrile to give 2.3 g. of 4-(p-methoxyphenyl)-2-(3-pyridyl)imidazole of m.p. 184-186.

B. 2-(3-pyridyl)-4-(4-hydroxyphenyl)imidazole

A mixture of 4-(p-methoxyphenyl)-2-(3-pyridyl-)imidazole (2.0 g.) and 48% HBr (100 ml.) is heated to reflux for 20 hrs. After cooling, the precipitate is filtered off and crystallized from isopropanol-methanol to give 2.05 g. of 2-(3-pyridyl)-4-(4-hydroxyphenyl)imidazole of m.p. 315°-318° C.

C. 4-[4-(3-tert-butylamino-2-hydroxypropoxy)phenyl]-2-(3-pyridyl)imidazole

A solution of 2-phenyl-3-tert-butyl-5-hydroxymethyloxazolidine (2.4 g., 0.01 m) in pyridine (3 ml.) is cooled to 0°-4° C. and treated portionwise with p-toluene-sulfonylchloride (2.0 g., 0.01 m). The cooled solution is slowly warmed to room temperature while not allowing the reaction mixture to exceed 30° C. After 2.5 hrs., the mixture is treated with a solution of $K_2CO_3$ (1.4 g.) in water (20 ml.) and extracted with chloroform (3×50 ml.). The organic layer is dried over $Na_2SO_4$, filtered, and concentrated to dryness under reduced pressure (20 mm) over steam and finally at 60° C. and 1 mm. The residual oil is dissolved in dry N,N dimethylformamide (DMF) (20 ml.) and added dropwise to a mixture of 2-(3-pyridyl)-4-(4-hydroxyphenyl-)imidazole:2HBr:$H_2O$ (4.0 g., 0.0095 m) in DMF (20 ml.) and sodium hydride (57% oil suspension, 1.3 g., 0.031 m). After refluxing for 11 hours, the mixture is concentrated to dryness under reduced pressure (1-2 mm Hg.) over steam. The residue is treated with 1N HCl (100 ml.), heated for ½ hr. on a steam bath, cooled, and extracted with ether. The aqueous layer is neutralized with 10N NaOH (12 ml.), extracted with $CHCl_3$ (3×50 ml.), dried over $Na_2SO_4$, filtered and concentrated to dryness.

The residue is chromatographed on No. 2 neutral alumina (200 g.) and eluted with 4% MeOH/$CHCl_3$. The crude product is further purified by chromatography on silica gel (200 ml.) and eluted with 40-50% MeOH/$CHCl_3$. The material is crystallized from acetonitrile to give 0.425 g. of 4-[4-(3-tert-butylamino-2-hydroxypropoxy)phenyl]-2-(3-pyridyl)imidazole of m.p. 163°-165° C.

EXAMPLE 42

Methyl 2-[4-(3-tert-butylamino-2-hydroxypropoxy)phenyl]-imidazole-4-carboxylate A solution of crude 2-[4-(3-tert-butylamino-2-hydroxypropoxy)phenyl]-4-carboxyimidazole ① (30 g.) in methanol (600 ml.) is heated to reflux, and then heating is discontinued as hydrogen chloride is bubbled rapidly through the solution with stirring for a half hour, followed by two and a half hours at reflux. Bubbling of hydrogen chloride is continued for another two hours followed by another hour at reflux and then the reaction mixture is stirred at room temperature overnight. The mixture is filtered and the filtrate is then concentrated to dryness under reduced pressure. The residue is dissolved in water (150 ml.) and the pH is adjusted to 8 with saturated sodium carbonate solution. The basic mixture is extracted with ethyl acetate and the extracts are dried, filtered, and concentrated under reduced pressure to yield a solid which is recrystallized from acetonitrile to yield the methyl 2-[4-(3-tert.butylamino-2-hydroxypropoxy)phenyl]-imidazole-4-carboxylate as a cream-colored solid, m.p. 168°-172° C.

①prepared from the corresponding 4-trifluoromethyl-imidazole per Example 39 procedure.

EXAMPLE 43

A. 2-[4-(3-Tert. butylamino-2-hydroxypropoxy)phenyl]-4-carbamoylimidazole

A solution of methyl 2-[4-(3-tert. butylamino-2-hydroxypropoxy)phenyl]imidazole-4-carboxylate (10 g.) in methanol (100 ml.) is reacted in a bomb with ammonia (44 g.) at 100° C. for 24 hours. The reaction mixture is concentrated under reduced pressure and the residue is chromatographed on silica gel. The product is eluted with chloroform that is washed with concentrated aqueous ammonia (90%) and methanol (10%) and is recrystallized from acetonitrile to yield the 2-[4-(3-tert. butylamino-2-hydroxypropoxy)phenyl]-4-carbamoylimidazole as a white solid, m.p. 149°-154° C.

B. 2-[4-(3-tert.-butylamino-2-hydroxypropoxy)phenyl]-4-cyanoimidazole

To a solution of 2-[4-(3-tert.-butylamino-2-hydroxypropoxy)phenyl]-4-carbamoylimidazole (0.5 g.) in dry pyridine (10 ml.) is added trifluoroacetic anhydride (1.26 g.) portionwise with stirring. The reaction solution is refluxed with stirring for four hours and then concentrated under reduced pressure. The residual gum is taken up in ethanol and saturated sodium carbonate solution (15 ml.) and stirred at room temperature for 20 hours. The ethanol is removed under reduced pressure and the remaining aqueous mixture is extracted with ethyl acetate. The extract is dried over sodium sulfate, filtered, and concentrated under reduced pressure. The residual glass is converted to its hydrochloride salt with ethanolic HCl and is recrystallized from ethanol-ether. The resulting tan solid is converted back to its free base by trituration with saturated sodium carbonate solution. The free base is extracted into ethyl acetate and the extract is dried over sodium sulfate, filtered and concentrated under reduced pressure. The residual gum is recrystallized from acetonitrile to yield 40 mg. of 2-[4-

(3-tert.-butylamino-2-hydroxypropoxy)phenyl]-4-cyanoimidazole, m.p. 174°-177° C.

EXAMPLE 44

A. 4-Hydroxy-5,6,7,8-tetrahydronapthaldehyde

Step A:

Dry hydrogen chloride gas is bubbled into a suspension of 5.0 gms. of 5,6,7,8-tetrahydronaphthol and 6.0 gm. zinc cyanide in 60 ml. of dry ethyl ether for two hours. To the mixture is added cautiously 50 ml. of water and 10 ml. 95% ethanol, and the resulting mixture is refluxed ½ hour. After cooling, the mixture is extracted with ethyl ether. The ether layer is washed with water and dried over anhydrous sodium sulfate. The ether is filtered and concentrated to an oil. The oil is dissolved in benzene, and 4-hydroxy-5,6,7,8-tetrahydronapththaldehyde crystallizes and is filtered.

B.

4-(2,3-Epoxypropoxy)-5,6,7,8-tetrahydronapthaldehyde

Step B:

To a solution of 4-hydroxy-5,6,7,8-tetrahydronapthaldehyde (20 gms., 0.012 m) in 1.5N sodium hydroxide (20 ml.) at 50° C. is added epichlorohydrin (3.3 gms., 0.036 m) dropwise). After 3 hours at 50° C., the solution is cooled and extracted with chloroform. The chloroform is dried over anhydrous sodium sulfate, filtered and concentrated to an oil. The oil is purified by column chromatography to give 2.4 gm. of 4-(2,3-epoxypropoxy)-5,6,7,8-tetrahydronapthaldehyde.

C.

4(3-tert.-Butylamino-2-hydroxypropoxy)-5,6,7,8-tetrahydronapthaldehyde

Step C:

To 4-(2,3-epoxypropoxy)-5,6,7,8-tetrahydronapthaldehyde (2.4 gms) is added tert.-butylamine (15 ml). The resulting solution is heated at 45° C. for 15 hours. The excess tert.-butylamine is removed at reduced pressure (20 mm). To the residue is added 30 ml. 6N hydrochloric acid, and the resulting mixture is refluxed for three hours. The acidic mixture is poured into a saturated solution of sodium carbonate which is heated on a steam bath with nitrogen bubbling through it. The basic mixture is extracted with chloroform, which is dried over anhydrous sodium sulfate, filtered and concentrated to give 2.3 g of 4-(3-tert.butylamino-2-hydroxypropoxy)-5,6,7,8-tetrahydronapthaldehyde as an oil.

D.

2-[(-3-tert.-Butylamino-2-hydroxypropoxy)-5,6,7,8-tetrahydronapthyl]-4-trifluoromethylimidazole Step D:

To sodium acetate trihydrate (2.07 gm., 0.015 m) in water (20 ml.) is added dibromotrifluoroacetone (2.07 g., 0.0075 m). The solution is heated for 40 minutes on a steam bath, cooled and added to a solution of 4-(3-tert.-butylamino-2-hydroxypropoxy)-5,6,7,8-tetrahydronapthaldehyde (2.3 mgs., 0.0075 m) in methanol (100 ml.) with concentrated aqueous ammonium hydroxide (15 ml.). The solution is allowed to stand at room temperature for 17 hours. The methanol is removed under reduced pressure (20 mm) over steam and ethyl acetate (100 ml.) and saturated aqueous sodium carbonate are added to the residue. The ethyl acetate is separated, dried of anhydrous sodium sulfate, filtered and concentrated. The oil is crystallized from acetonitrile to give 500 mg. of 2-[(3-tert-butylamino-2-hydroxypropoxy)-5,6,7,8-tetrahydronaphthyl]-4-trifluoromethylimidazole. Melting point 203°-205° C.

EXAMPLE 45

A. 4-(3-n-Butylamino-2-hydroxypropoxy)benzaldehyde

Step A:

To 4-(2,3-epoxypropoxy)benzaldehyde (8.9 gms., 0.05 m) is added n-butylamine (30 ml.) and the resulting solution is refluxed 17 hours. The excess n-butylamine is removed under reduced pressure (20 mm). The oil is dissolved in 6N hydrochloric acid (30 ml.) and the solution is heated on a steam bath for 40 minutes. The hot acidic solution is poured into a hot saturated aqueous sodium carbonate solution with nitrogen bubbling through it. The basic solution is extracted with chloroform. The chloroform is dried over sodium sulfate and concentrated to yield 4-(3-n-butylamino-2-hydroxypropoxy)benzaldehyde, as an oil.

B.

2-[4-(3-n-Butylamino-2-hydroxypropoxy)phenyl]-4-trifluoromethylimidazole

Step B:

To a solution of sodium acetate trihydrate (5.0 g.) in water (20 ml.) is added dibromotrifluoroacetone (5.0 g.). The solution is heated on a steam bath for 30 minutes. After cooling to room temperature, this solution is added to the methanolic solution of 4-(3-n-butylamino-2-hydroxypropoxy)-benzaldehyde and concentrated aqueous ammonium hydroxide (25 ml.). After standing at room temperature for 48 hours, the methanol is removed under reduced pressure (20 mm). The residue is dissolved in ethyl acetate and saturated aqueous sodium carbonate, dried over anhydrous sodium sulfate and concentrated under reduced pressure. The oil is placed in acetonitrile to yield 800 mg. of 2-[4-(3-n-butylamino-2-hydroxypropoxy)phenyl]-4-trifluoromethylimidazole, melting at 151°-154° C.

EXAMPLE 46

S-4-(4-methoxyphenyl)-2-[4-(3-tert-butylamino-2-hydroxypropoxy)-phenyl]-imidazole dihydrochloride dihydrate A heterogeneous solution of p-methoxyphenylglyoxal monohydrate (3.19 g. 0.018 m) sodium acetate (2.90 g., 0.036 m), water (23 ml), 37% aqueous ammonia (23 ml) and (S)-p-(3-tert-butylamino-2-hydroxypropoxy)-benzaldehyde (2.90 g., 0.012 m) in methanol (75 ml) is stirred at 25° C. for 72 hours. The reaction mixture is concentrated to dryness under reduced pressure (15 mm) at 80° C. The residual solid is treated with saturated aqueous $Na_2CO_3$ (75 ml), extracted with chloroform (4×75 ml), dried over anhydrous $MgSO_4$, filtered and concentrated to dryness. The residue is dissolved in chloroform (50 ml) and absorbed on an alumina pad (200 g). The pad is eluted with chloroform (2 l), 5% methanol/chloroform (1 liter), 10% methanol/-chloroform (l), 20% methanol/chloroform (l), 40% methanol/chloroform (1 l) and methanol (1 liter). Concentration of the 20% methanol/chloroform, 40% methanol/chloroform and methanol solutions gives 1.5 g of crude (S)-4-(4-methoxyphenyl)-2-[4-(3-tert-butylamino-2-hydroxypropoxy)-phenyl]-imidazole. This treatment of this crude product with 8N ethanolic hydrogen chloride (1 ml) yields the hydrochloride salt which is purified by three precipitations from isopropyl alcohol/ethyl acetate to give 810 mg of (S)-4-(4-methoxyphenyl)-2-[4-(3-tert-butylamino-2-hydroxy-propoxy)-phenyl]-imidazole dihydrochloride dihydrate; m.p. 132.0°-135.0° C.

EXAMPLE 47

A. 2,6-Dichloro-4-hydroxybenzaldehyde

To a stirred suspension of calcium hydroxide (61 gm), sodium carbonate (69.7 gm), and 3,5 dichlorophenol (20.97 gm) in water (436 ml) at 74° is added chloroform (45.3 gm) over 90 minutes. The solution is refluxed for 3½ hours. After the slow addition of concentrated hydrochloric acid (170 ml), the acidic solution is steam distilled the aqueous residue is cooled and the solid which separates is filtered. Recrystallization from toluene gives 1.1 gm of 2,6-dichloro-4-hydroxybenzaldehyde.

B. 2,6-Dichloro-4-(2,3-epoxypropoxy)benzaldehyde

To a stirred solution of 2,6-dichloro-4-hydroxy benzaldehyde (3.0 gm 0.0167 m) in 1.5N sodium hydroxide (25 m) at 50° is added epichlorohydrin (4.4 gm, 0.048 m). After stirring at 50° for 3 hours, the solution is cooled and extracted with chloroform. The chloroform is dried over anhydrous sodium sulfate, filtered and concentrated to 2,6-dichloro-4-(2,3-epoxypropoxy)-benzaldehyde (3 g) which is used without further purification.

C. 2,6-Dichloro-4-(3-tert-butylamino-2-hydroxypropoxy)-benzaldehyde

A mixture of 2,6-dichloro-4-(2,3-epoxypropoxy)-benzaldehyde (3 gm) and tert-butylamine (20 ml) is heated at 45° for 17 hours. The excess tert-butylamine is removed under reduced pressure (20 mm). The oil is dissolved in 6N hydrochloric acid (25 ml) and heated for 1 hour. The acid solution is added to boiling saturated aqueous sodium carbonate with nitrogen ebullition. The basic solution is extracted with chloroform. The chloroform is dried over anhydrous sodium sulfate, filtered and concentrated to 2,6-dichloro-4-(3-tert-butylamino-2-hydroxypropoxy)benzaldehyde which is used without further purification.

D. 2-[2,6-Dichloro-4-(tert-butylamino-2-hydroxypropoxy)phenyl]-4-trifluoromethyl imidazole A solution of sodium acetate trihydrate (2.7 gm 0.02 m) and dibromotrifluoroacetone (276 gm (0.01 m) in water (20 ml) is refluxed for 45 minutes. It is cooled and added to a solution of 2,6-dichloro-4-(3-tert-butylamino-2-hydroxypropoxy)benzaldehyde (3.0 gm, 0.009 m) in methanol (200 ml) and saturated aqueous ammonia (30 ml). After standing at room temperature for 17 hours, the solution is concentrated to an oil. The oil is dissolved in ethyl-acetate and washed with saturated aqueous sodium carbonate. The ethylacetate is dried over anhydrous sodium sulfate, filtered and concentrated. The gum is purified by chromatograph on silica gel with chloroform, washed with ammonium hydroxide and methanol as solvents. After purification 90 mg of 2-[2,6-dichloro-4(3-tert-butylamino-2-hydroxypropoxy)-phenyl]-4-trifluoromethyl imidazole is obtained.

EXAMPLE 48

1-Methyl-2-[4-(3-tert-butylamino-2-hydroxypropoxy)-phenyl]-4 (and 5)-trifluoromethyl imidazole An ether solution of diazomethane (1.5 gm) is added to a solution of 2-[4-(3-tert-butylamino-2-hydroxy-propoxy)phenyl]-4-trifluoromethylimidazole* in ether (100 ml) and methanol (50 ml). The solution is allowed to stand at room temperature until the yellow color has disappeared. The solvents are removed under reduced pressure. The resulting gum is chromatographed on silica gel with chloroform treated with aqueous ammonium hydroxide and methanol to yield 1-methyl-2-[4-(tert-butylamino-2-hydroxypropoxy)phenyl]-4-(and 5)-trifluoromethyl imidazole, which is a 50-50 mixture of the two N-methyl isomers.

*(1.7 gm)

ANALYSIS: NMR (d DMSO): N—$CH_3$ doublet. 3.72, 3.74. ($CH_3$)-tert-butyl 1.04. Mass spec: 371 m+ peak. 356 m-15.

EXAMPLE 49

2-[4-(3-dimethylamino-2-hydroxypropoxy)phenyl]-4-trifluoromethylimidazole

A solution of 2-[4-(2,3-epoxypropoxy)phenyl]-4-trifluoromethylimidazole in triethylamine (15 ml) is added 1.1 equivalents of a dimethylamine. This solution is refluxed until reaction is complete as indicated by TLC. The solvent is removed under reduced pressure and the residue recrystallized to yield 2-[4-(3-dimethylamino-2-hydroxypropoxy)phenyl]-4-trifluoromethylimidazole.

The methods illustrated in the examples 1-49 above are readily utilized to prepare other analogous imidazoles which are encompassed by the present invention.

EXAMPLE 50

S-2-[2-(3-tert. butylamino-2-hydroxypropoxy)-3-chloro-5-pyridyl]-4-trifluoromethylimidazole hydrogen maleate A. A mixture of 57% sodium hydride in mineral oil (0.53 g., equivalent to 0.30 g., 0.0126 m, of active sodium hydride) is added over a period of ten minutes to a stirred solution of S-2-phenyl-3-tert. butyl-5-hydroxymethyloxazolidine (2.97 g, 0.0126 m) in 25 ml of anhydrous toluene under nitrogen. The reaction mixture is allowed to stir at 25° C. for 15 minutes, 100° C. for 15 minutes and finally at 25° C. for 30 minutes. The homogeneous solution obtained is added dropwise over a period of 60 minutes to a rapidly stirred solution of 2,3-dichloro-5-cyanopyridine (2.0 g, 0.0126 m) in 20 ml of anhydrous toluene at 0° C. under nitrogen. The heterogenous reaction mixture is stirred rapidly at 0°-5° C. for 60 minutes and at 25° C. for 16 hours. This reaction mixture is then poured into 50 ml of water and the toluene layer separated. The aqueous phase is extracted with additional toluene 3×25 ml). The toluene extracts are combined, washed with saturated aqueous sodium chloride (50 ml), dried over anhydrous sodium sulfate, filtered and concentrated under reduced pressure (25 mm). The residue is diluted with 60 ml 1N aqueous hydrochloric acid and stirred on a steam bath for 5 minutes and at 25° C. for 30 minutes. The acidic reaction mixture is extracted with diethylether (5×50 ml) and chilled in an ice bath. 10M aqueous sodium hydroxide is added dropwise until the pH is approximately 12-14. The basic reaction mixture is extracted with chloroform (4×50 ml). The chloroform extracts are combined, dried over anhydrous sodium sulfate, filtered and concentrated at reduced pressure (25 mm). The remaining oil is dissolved in refluxing petroleum ether (400 ml), and on cooling to 25° C., 1.38 g of S-2-(tert. butylamino-2-hydroxypropoxy)-3-chloro-5-cyanopyridine is isolated melting at 62.0°–63.0° C.

B. A solution of S-2-(3-tert. butylamino-2-hydroxypropoxy)-3-chloro-5-cyanopyridine (11.19 g, 0.0394 m) in anhydrous toluene (100 ml) is stirred rapidly at −73° C. under nitrogen. A solution of diisobutylaluminum hydride in toluene (66.3 ml, (0.0394 m) of a 9.37M solution) is added dropwise over a ten minute period. The heterogeneous reaction mixture is stirred at −73° C. for 6 hours and then allowed to stand at 0° C. for 16 hours. The reaction mixture is stirred at 0° C. and treated dropwise with methanol (50 ml) followed by water (200 ml). The turbid solution is extracted with chloroform (3×200 ml). Chloroform extracts are combined, dried over anhydrous sodium sulfate, filtered and concentrated under reduced pressure (25 mm). The residual oil (11.4 g) is diluted with 60 ml of 6N aqueous hydrochloric acid and stirred at 100° C. for 30 minutes. The homogeneous acid solution is cooled to 0°–5° C. and treated with 10M aqueous sodium hydroxide until the pH is approximately 12–14. The basic solution is saturated with sodium chloride and extracted with chloroform (3×150 ml). The chloroform extracts are combined, dried over anhydrous sodium sulfate, filtered and concentrated at reduced pressure (25 mm) to yield 11.66 g of S-2-(3-tert. butylamino-2-hydroxypropoxy)-3-chloronicotinaldehyde as a light brown oil.

C. Sodium acetate (8.66 g., 0.0636 m) is treated with 60 ml of water and the homogeneous solution stirred rapidly at 25° C. Trifluorodibromoacetone (8.58 g, 0.0318 m) is added in one portion and the mixture heated at 100° C. for 40 minutes and cooled to 25° C. This solution is immediately added to a homogeneous mixture of S-2-(3-tert. butylamino-2-hydroxypropoxy)-3-chloronicotinaldehyde (6.09 g, 0.0212 m), methanol (150 ml) and concentrated aqueous ammonium hydroxide (60 ml). The reaction mixture is allowed to stir at 25° C. for 16 hrs., and concentrated at reduced pressure (25 mm) to remove the methanol. The aqueous solution is extracted with 3% methanol/chloroform (2×100 ml) and 5% methanol/chloroform (2×100 ml). All extracts are combined, dried over anhydrous sodium sulfate, filtered and concentrated at reduced pressure (25 mm) to yield 6.98 g of glassy foam. This foam is dissolved in absolute ethanol and the solution filtered through a 150 g silica pad. The filtrate is concentrated to a small volume, treated with a 10% excess of maleic acid and chilled. Upon dilution with diethyl ether, 1.82 g of S-2-[2-(3-tert. butylamino-2-hydroxypropoxy)-3-chloro-5-pyridyl]-4-trifluoromethylimidazole hydrogen maleate was isolated melting at 80.0°–85° C.

The free base may be obtained by conventional neutralization of the hydrogen maleate salt.

REACTION SCHEME FOR EXAMPLES A-D

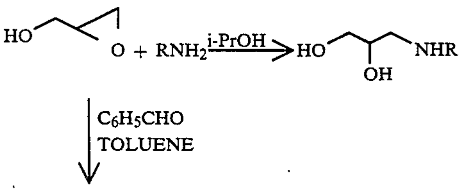

-continued

REACTION SCHEME FOR EXAMPLES A-D

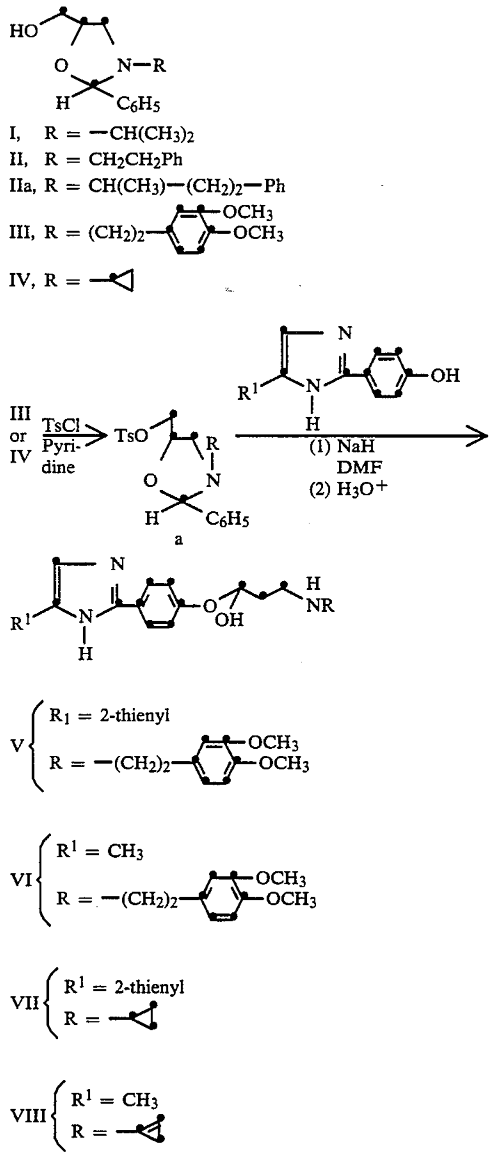

EXAMPLE A (a)

3-[2-(3,4-Dimethoxyphenyl)ethylamino]-1,1-propanediol, I

To a solution of β-(3,4-dimethoxyphenyl)ethylamine (151.0 g., 0.83 m) in isopropanol (160 ml.) heated at 50° is added a solution of glycidol (24.8 g., 0.33 m) in isopropanol (25 ml.) over 30 minutes. After heating at 50° for 30 minutes and at 70° for 15 hours, the solvent is concentrated under reduced pressure. The residue is distilled at 224°–227° C. at 0.7 mm. to yield I (47.9 g., 57%).

(b) 3-Cyclopropylamino-1,2-propanediol, II

To a solution of cyclopropylamine (95.2 g., 1.67 m.) in isopropanol (240 ml.) heated at 45° is added a solution of glycidol (50.0 g., 0.67 m.) over 30 minutes. The solution is heated at 50° for 30 minutes, at 70° for 1.5 hours and then stirred at 25° for 15 hours. The solvent is concentrated under reduced pressure and the residue is distilled at 116°-119° C. at 1.6 mm. to give II (87.8 g., 79%).

(c)
2-Phenyl-3-[2-(3,4-dimethoxyphenyl)ethyl]-5-(hydroxymethyl)oxazolidine, III

A mixture of I (47.9 g., 0.19 m.), benzaldehyde (44.6 g., 0.42 m) and benzoic acid (1 g.) in toluene (160 ml.) is refluxed for 3 hours, collecting the water formed in a Dean-Stark trap. After washing with saturated $NaHCO_3$ solution and saturated NaCl solution, the solvent is concentrated under reduced pressure. Excess benzaldehyde is removed by heating at 100° C. at 0.1 mm. The residue, III (65.2 g., 78%) is used without further purification.

(d)
2-Phenyl-3-cyclopropyl-5-(hydroxymethyl)oxazolidine, IV

Prepared by the same procedure as III, starting with II (69.0 g., 0.52 m.), benzaldehyde (200 ml., 1.98 m) and benzoic acid (3 g.) in toluene (110 ml.). The product, IV, is distilled at 130°-135° C. at 0.2 mm. (53.9 g., 47%).

2-phenyl-3-isopropyl-5-(hydroxymethyl)oxazolidine, 2-phenyl-3-(2-phenylethyl)-5-(hydroxymethyl)oxazolidine and 2-phenyl-3-(4-phenyl-2-butyl)-5-(hydroxymethyl)oxazolidine were prepared in the same manner as compound III using isopropylamine, 2-phenylethylamine and 4-phenyl-2-butylamine in place of 2-(3,4-dimethoxyphenyl)ethylamine.

(e)
2-{p-[[3-[2-(3,4-Dimethoxyphenyl)ethylamino]-2-hydroxypropoxy]]phenyl}-4-(2-thienyl)imidazole Dihydrochloride, V A solution of III (15.0 g., 0.044 m.) in pyridine (17 ml.) is cooled to 10° C. and p-toluenesulfonyl chloride (8.39 g., 0.044 m) is added over 30 minutes, keeping the temperature below 25° C. After stirring at 25° C. for 3 hours, a cold solution of $K_2CO_3$ (6.08 g., 0.044 m.) in $H_2O$ (40 ml.) is added and the mixture is extracted with $CHCl_3$ (3×75 ml.). The extracts are washed with $H_2O$, dried and concentrated under reduced pressure below 50° C., initially using water aspiration and finally high vacuum to yield the tosylate a (21.6 g., 99%). Sodium hydride (1.97 g., 0.041 m., 50% dispersion in mineral oil) is added to a solution of 2-(p-hydroxyphenyl)-4-(2-thienyl)imidazole (9.93 g., 0.04 (1 m.) in dimethylformamide (73 ml.) under nitrogen and the mixture is heated at 60° C. for 30 minutes. A solution of the tosylate (21.6 g., 0.043 mole) in dimethylformamide (65 ml.) is added and the mixture is refluxed for 17 hours. The solvent is distilled under reduced pressure, saturated sodium carbonate solution (125 ml.) is added and the mixture is extracted with ethyl acetate (2×150 ml.) and $CHCl_3$ (2×150 ml.). The combined organic layers are dried and concentrated under reduced pressure. The residue is heated on a steam bath for 1.5 hours with 1.5N HCl (400 ml.), cooled and extracted with ether (2×200 ml.). The acid layer is rendered alkaline with 20% NaOH solution and extracted with $CHCl_3$ (3×250 ml.). The solvent is evaporated under reduced pressure and the residue is chromatographed on silica gel and eluted with 5% MeOH-$CHCl_3$ saturated with $NH_3$. The product is isolated as the dihydrochloride salt and recrystallized from EtOH to give V (0.83 g., mp 278°-280° C.).

Anal. calcd. for $C_{26}H_{29}N_3O_4S.2HCl$: C, 56.52; H, 5.66; N, 7.61. Found: C, 56.57; H, 5.84; N, 7.46.

(f) Using 2-phenyl-2-isopropyl-5-(hydroxymethyl)oxazolidine, 2-phenyl-3-(2-phenylethyl)-5-(hydroxymethyl)oxazolidine and 2-phenyl-3-(4-phenyl-2-butyl)-5-hydroxymethyl)oxazolidine in place of III in step C gave the following products:

2-{p-[3-isopropylamino-2-hydroxypropoxy]phenyl}-4-(2-thienyl)imidazole; m.p. 172°-174° C.

2-{p-[3-(2-phenylethyl)amino-2-hydroxypropoxy]-phenyl}-4-(2-thienyl)imidazole-dihydrochloride; m.p. 274°-276° C.

2-{p-[3-(4-phenyl-2-butyl)amino-2-hydroxypropoxy]-phenyl}-4-(2-thienyl)imidazole dihydrochloride; m.p. 156°-166° C.

EXAMPLE B

4-Methyl-2-[p-[[3-[2-(3,4-dimethoxyphenyl)ethylamino]-2-hydroxypropoxy]]-phenyl]imidazole Dihydrochloride Hemihydrate, VI VI was prepared by essentially the same procedure as in Example A, starting with III (18.0 g., 0.052 m.) and 2-(p-hydroxyphenyl)-4-methylimidazole (8.36 g., 0.048 m). The product is isolated as the dihydrochloride salt and recrystallized from EtOH-ether to yield VI (2.07 g., mp 224°-227° C.).

Anal. Calcd. for $C_{23}H_{29}N_3O_4.2HCl.0.5H_2O$: C, 55.98; H, 6.54; N, 8.52; Cl, 14.37. Found: C, 55.87; H, 6.62; N, 8.32; Cl, 14.23.

EXAMPLE C

2-[p-(3-Cyclopropylamino-2-hydroxypropoxy)phenyl]-4-(2-thienyl)imidazole, VII

A solution of IV (6.80 g., 0.031 m.) in pyridine (12 ml.) is cooled to 10° C. and p-toluenesulfonyl chloride (5.91 g., 0.031 m) is added over 30 minutes, keeping temperature below 25° C. After stirring at 25° C. for 3 hours, a cold solution of $K_2CO_3$ (4.28 g., 0.031 m.) in $H_2O$ (28 ml.) is added and the mixture is extracted with $CHCl_3$ (3×50 ml.). The extracts are washed with $H_2O$, dried and concentrated under reduced pressure below 50° C., initially using water aspiration and finally high vacuum to yield the tosylate a (11.27 g., 97%). Sodium hydride (1.39 g., 0.029 m., 50% dispersion in mineral oil) is added to a solution of 2-(p-hydroxyphenyl)-4-(2-thienyl)imidazole (7.00 g., 0.029 m.) in dimethylformamide (50 ml.) under nitrogen and the mixture is heated at 60° C. for 30 minutes. A solution of the tosylate (11.27 g., 0.030 m.) in dimethylformamide (45 ml.) is added and the mixture is refluxed for 16 hours. The reaction mixture is poured into $H_2O$ (300 ml.) and extracted with ether (3×150 ml.). The combined organic layers are extracted with cold 1N HCl (3×75 ml.) and the acid layer added to sodium acetate (18.5 g., 0.23 m.) an stirred at 25° C. for 5 hours. The solution is extracted with ether (2X), basified with saturated $Na_2CO_3$ solution, extracted with 10% MeOH-$CHCl_3$ (3×150 ml.), 150 ml.), dried and concentrated under reduced pressure. The residue is chromatographed on silica gel and eluted with 5% MeOH-$CHCl_3$ saturated with $NH_3$. The product VII is crystallized from $CH_3CN$ (0.43 g., mp 169°-171.5° C.).

Anal. Calcd. for $C_{19}H_{21}N_3O_2S$: C, 64.20; H, 5.96; N, 11.82. Found: C, 63.90; H, 5.91; N, 11.71.

The dihydrochloride salt melts at 241.5°-243.5° C. after recrystallization from EtOH.

Anal. Calcd. for $C_{19}H_{21}N_3O_2S.2HCl$: C, 53.27; H, 5.41; N, 9.81. Found: C, 53.09; H, 5.45; N, 9.73.

EXAMPLE D

2-[p-(3-Cyclopropylamino-2-hydroxypropoxy)phenyl]-4-methylimidazole, VIII

Prepared by essentially the same procedure as VII, starting with III (32.08 g., 0.146 m.) and 2-(p-hydroxyphenyl)-4-methylimidazole (24.4 g., 0.14 m.). The free base VIII (1.44 g.) is recrystallized from $CH_3CN$. An analytical sample melts at 150.5°-153.5° C.

Anal. Calcd. for $C_{16}H_{21}N_3O_2$: C, 66.87; H, 7.37; N, 14.62. Found: C, 66.63; H, 7.45; N, 14.25.

The dihydrochloride salt melts at 244.5°-245.5° C. (d) after recrystallization from EtOH.

Anal. Calcd. for $C_{16}H_{21}N_3O_2.2HCl$: C, 53.34; H, 6.43; N, 11.66. Found: C, 53.37; H, 6.59; N, 11.38.

EXAMPLE E

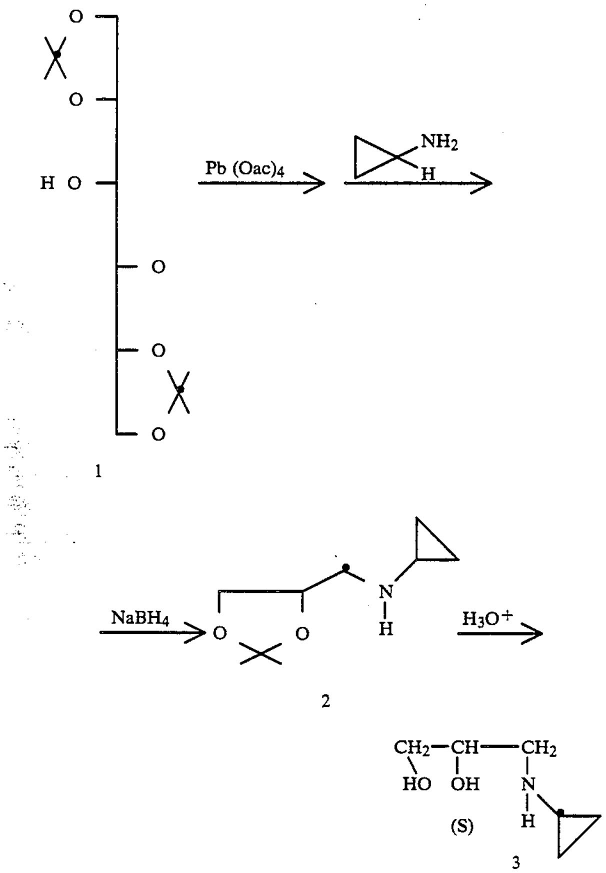

1

2

3

(a) (S) 3-cyclopropylamino-1,2-propanediol(3)

To an ice cooled solution of 1 (96 g., 0.37 mol.) in THF (450 ml.) was added portionwise with stirring dry $Pb(OAc)_4$ (164 g., 0.37 mol.) while maintaining the temperature below 10° C. The solution was stirred for 30 minutes at 0°-5° C. and additional 30 minutes at room temperature. The mixture was filtered through Super-Cel, the pad washed with THF and the cooled yellow solution treated with cyclopropylamine (96 ml., 79 g., 1.38 mol). After the addition, the reaction mixture was stirred for one hour at room temperature, cooled to 0°, and a solution of $NaBH_4$ (28 g., 0.74 mol.) in EtOH (800 ml.) was added with vigorous stirring while keeping the temperature below 10° C. After the addition, the mixture was stirred for 1½ hours at room temperature, 4% NaOH (500 ml.) added and the pH adjusted to 9.4 with solid $NH_4Cl$. The mixture was filtered and the filtrate was concentrated to remove the organic solvents. The aqueous layer was extracted with $CH_2Cl_2$ (7X). The organic extracts were dried, filtered and concentrated to dryness to yield 121 g. of 2. Crude 2 was treated with cold 1N HCl (800 ml.) and stirred at room temperature for 2 hours. The solution was then neutralized with solid $K_2CO_3$ and saturated with NaCl. The resulting solution was continuously extracted with $CHCl_3$ for 5 days to yield 3. After distillation $bp_{0.3}$ 95°-100° C., 46.7 g. of 3 (48%) were obtained; 'H NMR ($CDCl_3$) 0.4 (4H, m), 2.15 (1H, m), 2.75 (2H, m), 3.6 (6H, m); $\alpha^{25}_D = -30.7$ (1N HCl).

C=1.22.

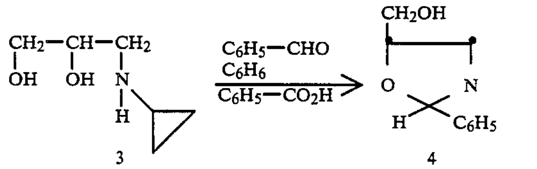

3 4

(b) (S) 2-phenyl-3-cyclopropyl-5-hydroxymethyloxazolidine (4)

A solution of 3 (46 g., 0.35 ml.), benzoic acid (1.5 g.), benzaldehyde (120 ml.) and $C_6H_6$ (75 ml.) was heated to reflux while collecting the $H_2O$ in a Dean-Stark trap. After 1 hour, a theoretical amount of $H_2O$ was collected and the solution was poured into cold $H_2O$ (200 ml.) containing $NaHCO_3$ (9 g.) and NaCl (24 g.). The layers were separated and the aqueous layer extracted with $CHCl_3$ (2X). The combined extracts were dried, filtered concentrated to dryness, and the residue distilled at $bp_{0.3}$ 125°-130° C. to yield 57.4 g. (75%) of 4; 'H NMR ($CDCl_3$) 0.25 (4H, m), 1.8 (1H, m), 3.05 (3H, m), 3.7 (2H, m), 4.25 (1H, m), 5.1 (1H, d), 7.3 (5H, bs).

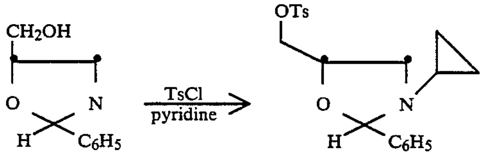

4 5

(c) (S) 2-phenyl-3-cyclopropyl-5-hydroxymethyl-oxazolidine-5-(p-methylphenylsulfonate) (5)

To a solution of 4 (72 g., 0.33 mol.) in $C_5H_5N$ (145 ml.) was added portionwise p-toluene-sulfonylchloride (63 g., 0.33 mol.) while maintaining the temperature below 10° C. After completion of this addition, the mixture was maintained at −5° to 0° C. After 4 hours, a cold solution of $K_2CO_3$ (46 g., 0.33 mol.) in $H_2O$ (285 ml.) was added and the mixture extracted with $CHCl_3$ (3X). The organic extracts were dried, filtered and concentrated to dryness to yield a quantitative yield of 5; 'H NMR ($CDCl_3$) 0.25 (4H, m), 1.85 (1H, m) α 4 (3H, s), 3.15 (2H, m), 4.1 (3H, m), 5.05 (1H, s), 7.4 (9H, m)

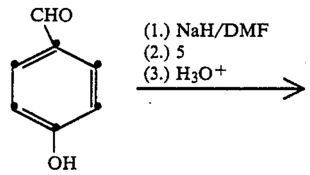

6

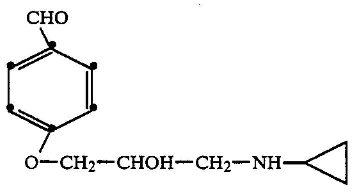

7

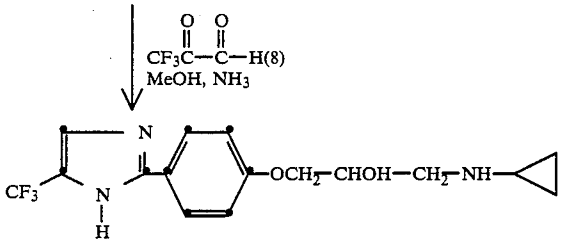

9

(d) (S) 2-[4-(3-cyclopropylamino-2-hydroxypropoxy)phenyl]-4-trifluoromethylimidazole (9)

To a suspension of NaH (60% oil dispersion, 15.2 g., 0.38 mol.) in DMF (350 ml.) under $N_2$ was added 6 (40.3 g., 0.33 mol.) and the mixture heated at 70° C. with stirring. After 15 minutes, a solution of 5 (123 g., 0.33 mol.) in DMF (200 ml.) was added dropwise. After the addition, the reaction mixture was heated at 120° C. for 18 hours. The mixture was then poured onto ice and extracted with EtOAc (4X). The organic layer was washed with solid $Na_2$-$CO_3$, $H_2O$, dried, filtered and concentrated to dryness. The residue was stirred in $H_2O$ (1 l) and AcOH (80 ml.). After stirring at room temperature overnight, the solution was extracted with EtOAc (2X) and the aqueous layer poured into saturated $Na_2$-$CO_3$. The basic solution was then extracted with $CHCl_3$ (4X) and the organic layer dried, filtered and concentrated to dryness to yield 50 g. of crude 7 which were added to a solution of 8 (0.21 mol.) in $H_2O$ (210 ml.) along with $CH_3OH$ (800 ml.) and 28% aqueous $NH_3$ (270 ml.). The mixture was stirred at room temperature overnight and then the $CH_3OH$ was removed under reduced pressure. The resulting aqueous layer was basified with saturated $Na_2CO_3$ and extracted with $CHCl_3$ (4X). The organic layers were dried, filtered and concentrated to dryness. The residue was chromatographed on silica gel and the product eluted with 5% $CH_3OH$—$CH_2Cl_2$ saturated with $NH_3$. The product was crystallized from $H_3CCN$ to yield 14.2 g. of 9. Recrystallization from $H_3CCN$ yielded 13.7 g. of 9 (25%); mp 169°-171° C.; $\alpha_D^{25}=-11.83°$ C=1.851 (1N HCl); 'H NMR ($CDCl_3$) 0.3 (4H, m), 2.05 (1H, m), 2.7 (2H, m), 3.9 (3H, m), 7.0 (2H, d), 7.85 (3H, d and s).

EXAMPLE F

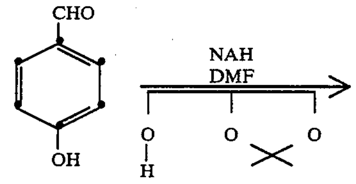

1 2

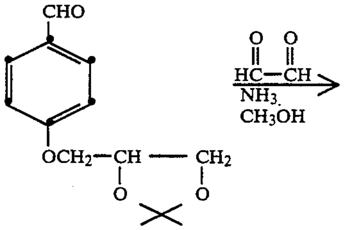

3

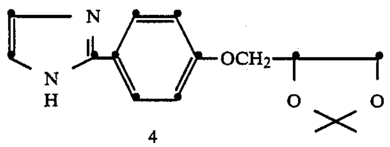

4

(a) p-(2-imidazolyl)phenoxy-1,2-propanediol acetonide(4)

To a suspension of NaH (60% oil dispersion, 10 g., 0.25 mol.) in DMF (50 ml.) was added dropwise under $N_2$ at 70° C. a solution of 1 (28 g., 0.23 mol.) in DMF (150 ml.). After 15 minutes at 70° C., a solution of 2 (45.5 g., 0.22 mol.) in DMF (50 ml.) was added dropwise. After heating on a steam bath for 18 hours, $H_2O$ was added and the solution extracted with EtOAc (3X). The combined extracts were washed with $H_2O$ (2X), saturated NaCl, dried, filtered and concentrated to dyrness to yield crude 3. To 3 was added $CH_3OH$ (500 ml.), 40% glyoxal (100 ml.) and 28% concentrated aqueous $NH_3$. After stirring overnight at room temperature, the $CH_3OH$ was removed under reduced pressure, $H_2O$ added to the residue and the aqueous solution extracted with $CHCl_3$ (4X). The combined extracts were dried, filtered and concentrated to dryness. The residue chromatographed on silica gel and the product eluted with 10% $CH_3OH$—$CHCl_3$ to yield 4. Concentration of the solvent and trituration with hexane yielded 18 g. of 4. The product was crystallized from toluene-ligroin to yield 13 g. of 4 (22%); mp 148°-150°; 'H NMR (DMSO-$d_6$) 1.35 (6H, d), 4.0 (5H, m), 6.95 (2H,d), 7.05 (2H, s), 7.8 (2H, d).

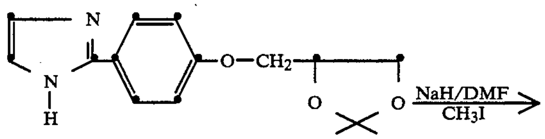

4

-continued

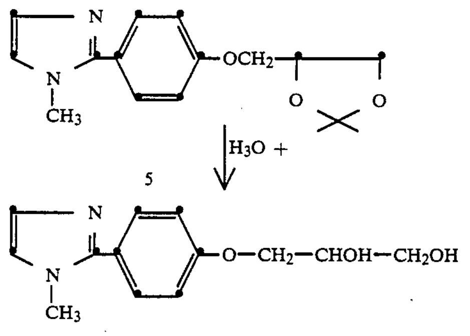

5

6

(b) p-(N-methyl-2-imidazolyl)phenoxy-1,2-propanediol 6

Into a flamed out flask under $N_2$ was added NaH (60% oil dispersion, 6.0 g, 0.15 mol), DMF (750 ml.) and 4 (41.6 g., 0.15 mol.). The solution was cooled to 0°-5° C. and a solution of $CH_3I$ (23.4 g., 10.2 ml., 0.165 mol.) in DMF (75 ml.) was added. The reaction mixture was stirred overnight while allowing the ice bath to attain room temperature. After 18 hours, the reaction mixture was poured in $H_2O$ (3 l) and extracted with EtOAc (4X).

The combined extracts were washed with $H_2O$, saturated NaCl, dried, filtered and concentrated to dryness to yield 5. 5 'H NMR ($CDCl_3$) 1.45 (6H, d), 3.6 (3H, s), 4.0 (5H, m), 6.95 (4H, d, 2S), 7.5 (2H, d). The residue was treated with 3N HCl (200 ml.), and acetone (200 ml.) heated on a steam bath for ½ hour, cooled, extracted with EtOAc (2X), and poured onto solid $K_2CO_3$. The saturated aqueous solution was extracted with $CHCl_3$, (4X). The combined extracts were dried, filtered and concentrated to dryness. The residue was triturated with $Et_2O$ to yield 23.4 g. of 6 (65%). 6 'H NMD D(DMSO-$d_6$) 3.4 (2H, m), 3.65 (3H, s), 3.9 (3H, m), 4.8 (2H, exch), 7.0 (1H, s), 7.1 (2H, d), 7.2 (1H, s), 7.6 (2H, d).

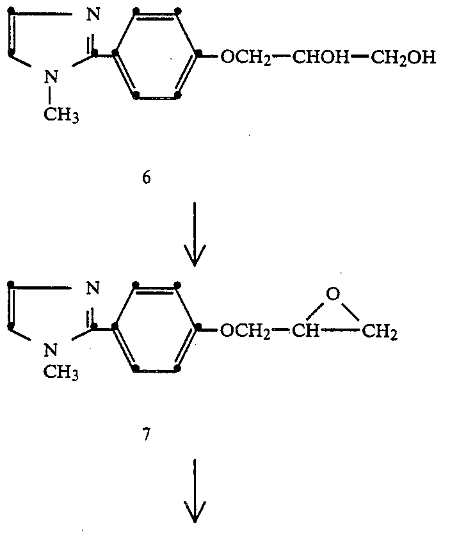

6

7

-continued

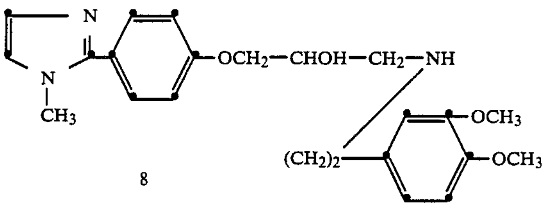

8

(c) p-(N-methyl-2-imidazolyl)phenoxy-1,2-epoxypropane (7)

Into a flask under $N_2$ was placed 6 (7.0 g., 0.03 mol.), pyridine (20 ml.), pyridine.HCl (3.9 g., 0.034 mol.) and the mixture cooled in an ice bath. To the cooled mixture was added methanesulfonyl chloride (3.26 g., 2.2 ml., 0.028 mol.). After 10 minutes, $Et_2O$ (130 ml.) $NaOCH_3$ (19 g., 0.35 mol.), and $CH_3OH$ (65 ml.) were added and the suspension stirred for ½ hour. Water was added and the layers were separated. The aqueous layer was further extracted with $CH_2Cl_2$ (3X). The combined extracts were washed with $H_2O$, saturated NaCl, dried, filtered and concentrated to dryness to yield 7; 'H NMR ($CDCl_7$) 2.8 (2H, m), 3.3 (1H, m), 3.65 (3H, s), 4.1 (2H, m), 7.4 (6H, m).

(d) 2-[p-[[3-[2-(3,4-dimethoxyphenyl)ethylamino]]-2-hydroxypropoxy]phenyl]-N-methyl imidazole.2HCl(8)

Compound 7 was dissolved in isopropanol (45 ml) and a solution of 3,4-dimethoxyphenethylamine (4.5 g., 0.025 ml.) was added dropwise. After the addition the solution was heated with stirring at 70° C. After 18 hours, the solution was concentrated to dryness. The residue was chromatographed on silica gel and the product eluted with $CHCl_3$ saturated with $NH_3$. The product was crystallized from HCl/EtOH and recrystallized from isopropanol to yield 2.7 g. of 8, mp 192°-194° C.; 'H NMR (DMSO-$_6$) 3.05 (6H, m), 3.7 (6H, d), 3.85 (3H, s), 4.3 (3H, m), 6.8 (3H, m), 7.2 (2H, d), 7.8 (4H, m).

EXAMPLE G

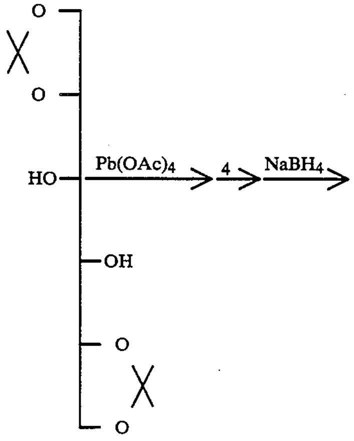

1

-continued

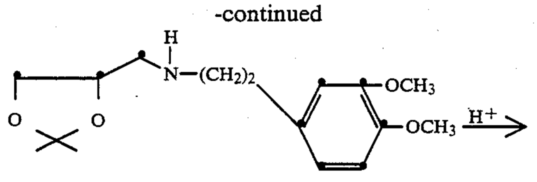

2

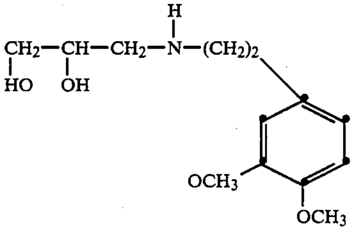

(S)-3

(a) (S) 3-[2-(3,4-dimethoxyphenyl)ethylamino]-1,2-propanediol (3)

To an ice cooled solution of 1 (128.7 g, 0.49 mol.) in THF (650 ml.) was added portionwise with stirring dry $Pb(OAc)_4$ (220 g., 0.5 mol.) while maintaining the temperature below 10° C. The solution was stirred for 30 minutes at 0°-5° C. and an additional 30 minutes at room temperature. The mixture was filtered through Super-Cel, the pad washed with THF (500 ml.d) and the yellow cooled solution treated with 3,4-dimethoxyphenethylamine 4 (331 g., 1.8 mol.). After the addition, the thick suspension was stirred for 1 hour at room temperature, cooled to 0°, and a solution of $NaBH_4$ (13.1 g., 0.34 mol.) in 9% NaOH (600 ml.) was added with vigorous stirring while keeping the temperature below 10° C. After the addition stir for ½ hour at 0°-4°, 1½ hour at room temperature, and then the pH of the solution adjusted to 9.4 with solid $NH_4Cl$. The organic solvents were concentrated and the resulting solution extracted with $CHCl_3$ (3×). The combined extracts were dried, filtered and concentrated to dryness to yield 482 g. of 2. Crude 2 was treated with cold 2N HCl (1 l) and stirred at room temperature. After 18 hours, the solution was neutralized with solid $K_2CO_3$, extracted with EtOAc, and saturated with solid NaCl. The resulting solution was continuously extracted for 5 days with $CHCl_3$ to yield 360 g. of 3 and 4. The residue was chromatographed on silica gel and eluted with 5% MeOH-$CHCl_3$ saturated with $NH_3$ to yield 138.3 g. of 4 (90% recovery) and then with 10-20% MeOH-$CHCl_3$ saturated with $NH_3$ to yield 195 g. of 3 (77%). The residue triturated with hexane yielded a solid, mp=52°-56°, $[\alpha]_D^{25}=-16.48$ (1N HCl) C=2.055; 40 1H NMR 2.7 (6H, m), 3.0 (3H, bs), 3.6 (2H, bs), 3.8 (7H, d, m), 6.7 (3H, bs).

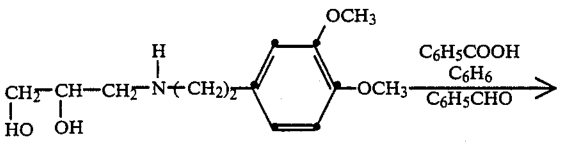

(S)-3

-continued

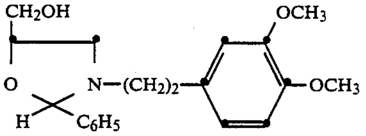

5

(b) (S) 2-phenyl-3-[2-(3,4-dimethoxyphenyl)ethyl]-5-hydroxymethyloxazolidine (5)

A solution of 3 (195 g., 0.76 mol.), benzoic acid (3.0 g.), benzaldehyde (270 ml.), $C_6H_6$ (180 ml.) was heated to reflux while collecting the $H_2O$ in a Dean-Stark trap. After 2½ hours, 13 ml. of $H_2O$ was collected and the solution cooled, washed with saturated $Na_2CO_3$. The aqueous layer was washed with $CHCl_3$ (2×) and the combined extracts dried, filtered and concentrated to dryness to yield 232 g. of 5 which contains 26 mol% benzaldehyde. This corresponds to 209 g. of 5; 'H NMR ($CDCl_3$) 2.6 (6H, m), 3.4 (2H, m), 3.75 (7H, d, m), 4.3 (1H, m), 4.8 (1H, d), 6.7 (3H, m), 7.4 (5H, bs).

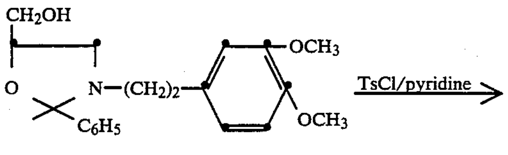

1

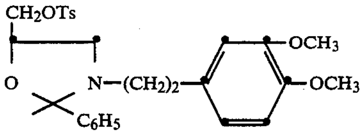

2

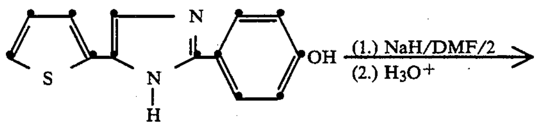

3

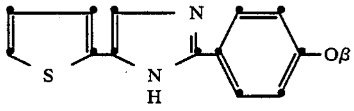

4

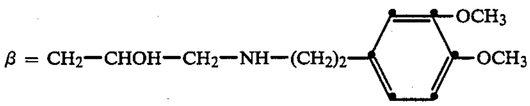

(c) 2-phenyl-3-[2-(3,4-dimethoxyphenyl)ethyl]-5-hydroxymethyloxazolidine-5-(p-methylphenylsulfonate) (2)

To a solution of 1 (34.3 g., 0.1 mol.) in pyridine (45 ml.) cooled to 0°-5° C. was added portionwise p-toluenesulfonyl chloride (19.3 g., 0.1 mol.) while maintaining the temperature below 30° C. After 3 hours at 0°-5° C., $CHCl_3$ was added and the solution washed with saturated $Na_2CO_3$. The aqueous layer was further extracted with $CHCl_3$ (2×) and the combined extracts dried over $Na_2SO_4$, filtered and concentrated first at 20 mm pressure and then at 1 mm while keeping the temperature below 50° C. to yield 2 as an oil.

(d) (S) 2-{p-[[3-[2-(3,4-dimethoxyphenyl)ethylamino]-2-hydroxypropoxy]]phenyl}-4-(2-thienyl)imidazole.2HCl (4)

To a suspension of NaH (60% oil dispersion, 4.8 g., 12 mol.) in DMF (120 ml.) was added at 70° C. under $N_2$ a solution of 3 (23 g., 0.095 mol.) in DMF (120 ml.). After stirring for 15 minutes at 70° C. a solution of 2 in DMF (120 ml.) was added dropwise. After the addition, the mixture was heated at 120° C. for 18 hours. The solution was then concentrated to dryness at 0.1 mm. of pressure and the residue treated with AcOH (100 ml.) 3N HCl (30 ml.) and $H_2O$ (1 l). After stirring overnight, the solution was extracted with EtOAc (2×) and the aqueous layer adjusted to pH 10 with saturated $Na_2CO_3$ and extracted with $CHCl_3$ (4×). The organic layers were dried, filtered and concentrated to dryness. The residue was chromatographed on silica gel and the product eluted with 5% MeOH-$CHCl_3$ saturated with $NH_3$ to yield 8.5 g. of 4 which was crystallized from $H_3CCN$ to yield 5.5 g. of 4 (11%); mp 127°-129° C.

The sample was converted to the dihydrochloride salt by crystallization from HCl-EtOH. Recrystallization from EtOH yielded 4. 2HCl; mp 269°-274° C.; $[\alpha]_D^{25} = -7.3$, C=1($H_2O$); 'H NMR (DMSO) 3.05 (7H, m, 1 exch), 3.7 (6H, d), 4.3(5H, m, 1 exch), 6.83 (3H, bs), 7.2 (3H, m), 7.67 (1H, d), 7.97 (2H, bs), 8.37 (2H, d), 9.27 (2H, bs, exch).

In the above sequence, using (S) 2-phenyl-3-cyclopropyl-5-Hydroxymethyl-oxazolidine-5-(p-methylphenylsulfonate in place of 2 gave (S) 2-{3-cyclopropylamino-2-hydroxypropoxy)phenyl}-4-(2-thienyl-)imidazole dihydrochloride instead of 4. $[\alpha]_D^{25} = -10.7°$, mp=238°-241°.

EXAMPLE H

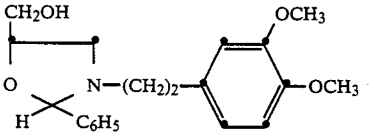

(S)-1

-continued

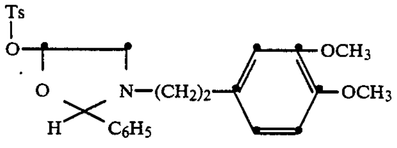

(S)-2

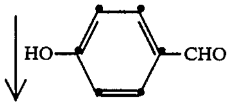

3

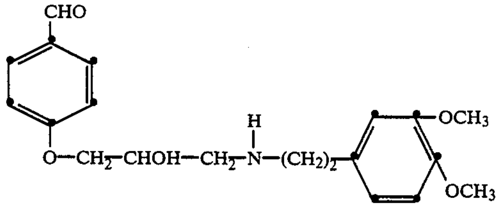

(S)-4

(a) To a solution of (S) 1 (10.3 g., 0.03 mol.) in pyridine (15 ml.) cooled to 0°-5° C. was added portionwise a solution p-toluenesulfonyl chloride (5.7 g., 0.03 mol.) while maintaining the temperature below 30° C. After 4 hours at room temperature, $CHCl_3$ was added and the solution washed with saturated $Na_2CO_3$. The aqueous layer was further extracted with $CHCl_3$ (2×) and the combined extracts dried over $Na_2SO_4$, filtered and concentrated first at 20 mm pressure and then at 1 mm while keeping the temperature below 50° C. to yield (S) 2.

(b) (S) p-[3-[2-(3,4-dimethoxyphenyl)ethyl]-2-hydroxypropoxy]benzaldehyde (4)

To a suspension of NaH (60% oil dispersion, 1.2 g., 0.03 mol.) in DMF (20 ml.) was added at 70° C. under $N_2$ a solution 3 (37 g., 0.03 ml.) in DMF (30 ml.). After stirring for 15 minutes at 70° C. a solution of (S) 2 in DMF (50 ml.) was added dropwise. After the addition, the mixture was heated at 120° C. for 18 hours. The solution was then poured into $H_2O$ and extracted with EtOAc (3×). The organic extracts were washed with $H_2O$ (2×), saturated NaCl (1×), dried, filtered and concentrated to dryness. The residue was treated with $H_2O$ (250 ml.) and AcOH (25 ml.) and stirred overnight at room temperature. The solution was extracted with EtOAc (2×), neutralized with saturated $Na_2CO_3$ and extracted with $CHCl_3$ (9×). The organic extracts were dried, filtered and concentrated to yield 8.5 g. of 4; 'H NMR ($CDCl_3$) 2.7 (6H, m), 3.8 (6H, s), 4.1 (3H, m), 6.7 (3H, bs), 6.95 (2H, d), 7.75 (2H, d).

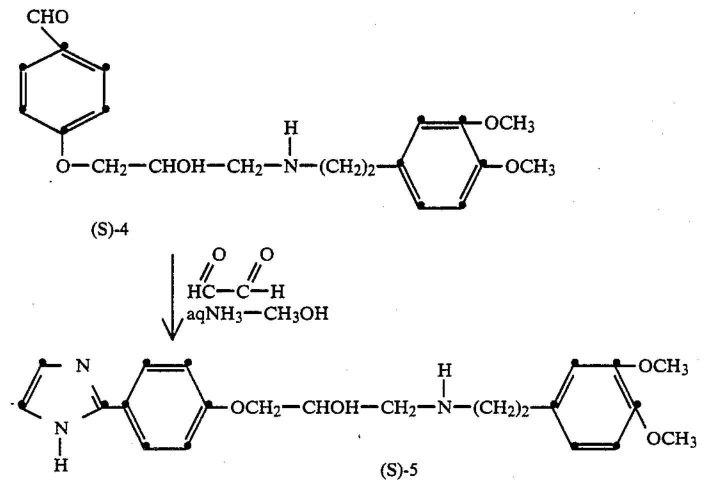

(S)-4

(S)-5

(c) (S) 2-[p-[[3-[2-(3,4-dimethoxyphenyl)ethylamino]-2-hydroxypropoxy]phenyl]]imidazole.2HCl.$H_2O$ (5)

A mixture of (S) 4 (8.5 g., 0.024 mol.), $CH_3OH$ (50 ml), 40% glyoxal (10 ml., 0.069 mol.), 28% concentrated aqueous $NH_3$ (15 ml.) was allowed to stir at room temperature. After 18 hours, the $CH_3OH$ was removed under reduced pressure and water added (100 ml.). The aqueous layer was extracted with $CHCl_3$ (4×) and the organic layer dried, filtered and concentrated to dryness. The residue was chromatographed on silica gel and the product eluted with 2% $CH_3OH$—$CHCl_3$ saturated with $NH_3$ to yield 3.0 g. of (S) 5 which was converted to the dihydrochloride salt by crystallization from HCl-EtOH. Recrystallization from isoPrOH-$CH_3OH$ yielded 1.3 g. of (S) 5 (11%); mp 223°-25° C.; $[\alpha]_D^{25}=-6.94$ ($H_2O$) (C=0.502) H NMR (DMSO-$d_6$) 3.2 (6H, m), 3.8 (6H, d), 4.2 (3H, d), 6.9 (3H, m), 7.25 (2H, d), 7.75 (2H, s), 8.35 (2H, d), 9.35 (2N, bs, exch).

Preparation of 2-[[p-[3-[2-(3,4-Dimethoxyphenyl)ethylamino]-2-hydroxypropoxy]phenyl]]imidazole, III, and 2-[p-(3-Cyclopropylamino-2-hydroxypropoxy)phenyl-]imidazole, IV

REACTION SCHEME FOR EXAMPLE J

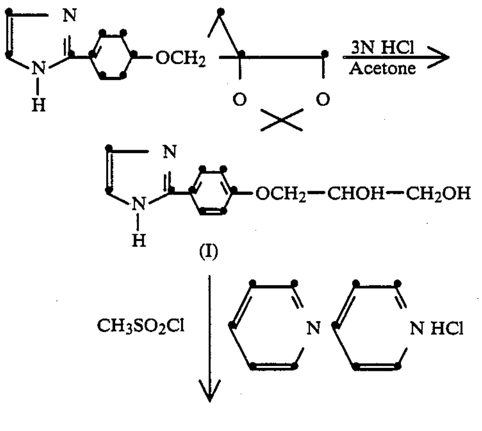

(I)

-continued

REACTION SCHEME FOR EXAMPLE J

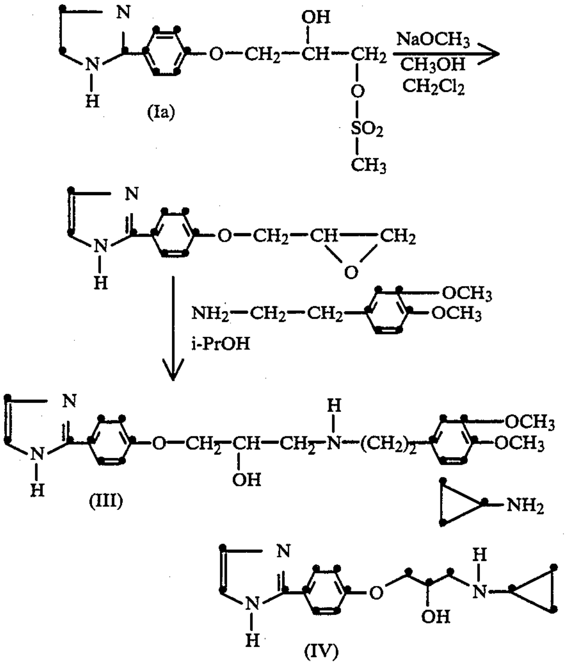

(Ia)

(III)

(IV)

EXAMPLE J (a) 3-[p-(2-Imidazolyl)phenoxy]-1,2-propanediol, I

A mixture of 3-[p-(2-imidazolyl)phenoxy]-1,2-propanediol acetonide (5.9 g., 0.022 m.) in 3N HCl (45 ml.) and acetone (45 ml.) is refluxed for 0.5 hours. Acetone is removed under reduced pressure and the aqueous mixture is rendered alkaline with $K_2CO_3$. The solid is collected and dried in a vacuum oven at 55° to yield (I) (5.2 g., 100%, m.p. 165.5°-167°).

(b) 3-[p-(2-Imidazolyl)phenoxy]-1,2-epoxypropane, (II)

A mixture of 3-[p-(2-imidazolyl)phenoxy]-1,2-propanediol (15.19 g., 0.065 m.), pyridine hydrochloride (8.2 g., 0.071 m.) and pyridine (125 ml.) is cooled in an ice-salt bath and stirred while methanesulfonyl chloride (7.45 g., 0.065 m.) is added over 15 minutes. The mixture is stirred at room temperature for 1.5 hours, then a cold solution of $K_2CO_3$ (9.0 g., 0.065 m) in $H_2O$ (30 ml.) is added and the mixture is concentrated at 50° under high vacuum. The residue is treated with another solution of $K_2CO_3$ (9.0 g.) in $H_2O$ (50 ml.) and slurried until a gummy solid forms. The crude monomesylate (Ia) is dried in the vacuum oven at 45° to yield a yellow solid weighing 18.34 g. (90%).

The crude mesylate is suspended in a mixture of methanol (215 ml.) and methylene chloride (215 ml.) and cooled to 0° while a solution of sodium methoxide (3.51 g., 0.065 m.) in methanol (40 ml.) is added over 10 minutes with stirring. After stirring at 0° for 1.5 hours, $H_2O$ (100 ml.) is added and the organic layer is separated. The aqueous layer is extracted with $CH_2Cl_2$ (250 ml.) and the combined organic layers are dried and the solvent is concentrated under reduced pressure to yield (II) as a yellow solid (10.26 g., 73%) which is used without further purification.

(c)

2-{p-[[3-[2-(3,4-Dimethoxyphenyl)ethylamino]-2-hydroxypropoxy]phenyl]}-imidazole, (III)

A mixture of 3-[p-(2-imidazolyl)phenoxy]-1,2-epoxypropane (1.00 g., 0.0046 m.) and 2-(3,4-dimethoxyphenyl)ethylamine (1.25 g., 0.0069 m.) in isopropanol (20 ml.) is stirred at 70° for 19 hours. The solvent is evaporated under reduced pressure and the residue is chromatographed on silica gel, eluting with 5% MeOH-$CHCl_3$ saturated with $NH_3$. The free base III (0.58 g., 32%) is crystallized as the dihydrochloride salt from EtOH-MeOH-ether (m.p. 233.5°-23.5°).

Anal. Calcd. for $C_{22}H_{27}N_3O_4.2HCl$: C, 56.17; H, 6.21; N, 8.93; Cl, 15.08. Found: C, 55.89; H, 6.22; N, 8.55; Cl, 14.91.

(d)

2-[p-(3-Cyclopropylamino-2-hydroxypropoxy)phenyl-]imidazole, (IV)

A mixture of 3-[p-(2-imidazolyl)phenoxy]-1,2-epoxypropane (4.95 g., 0.023 m.) in cyclopropylamine (50 ml.) is refluxed at 60° for 30 hours. The mixture is concentrated under reduced pressure and the residue is chromatographed on silica gel, eluting with 5-10% MeOH-$CHCl_3$ saturated with $NH_3$. The free base (IV) (1.21 g., 19%) is crystallized as the dihydrochloride salt from EtOH-MeOH-ether (m.p. 214°-5°).

Anal. Calcd. for $C_{15}H_{19}N_3O_2.2HCl$: C, 52.03; H, 6.11; N, 12.14. Found: C, 51.71; H, 6.24; N, 11.94.

EXAMPLE K

Preparation of

2-[p-[[3-[3-(3,4-Dimethoxyphenyl)-2-methyl-2-propylamino]-2-hydroxypropoxy]]phenyl]-4-(2-thienyl-)imidazole, (VI), and 2-[p[[3-[3-(3,4-Dimethoxyphenyl)-2-propylamino]-2-hydroxypropoxy]]phenyl]-4-(2-thienyl)imidazole, (VII)

REACTION SEQUENCE

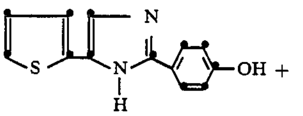

-continued

REACTION SEQUENCE

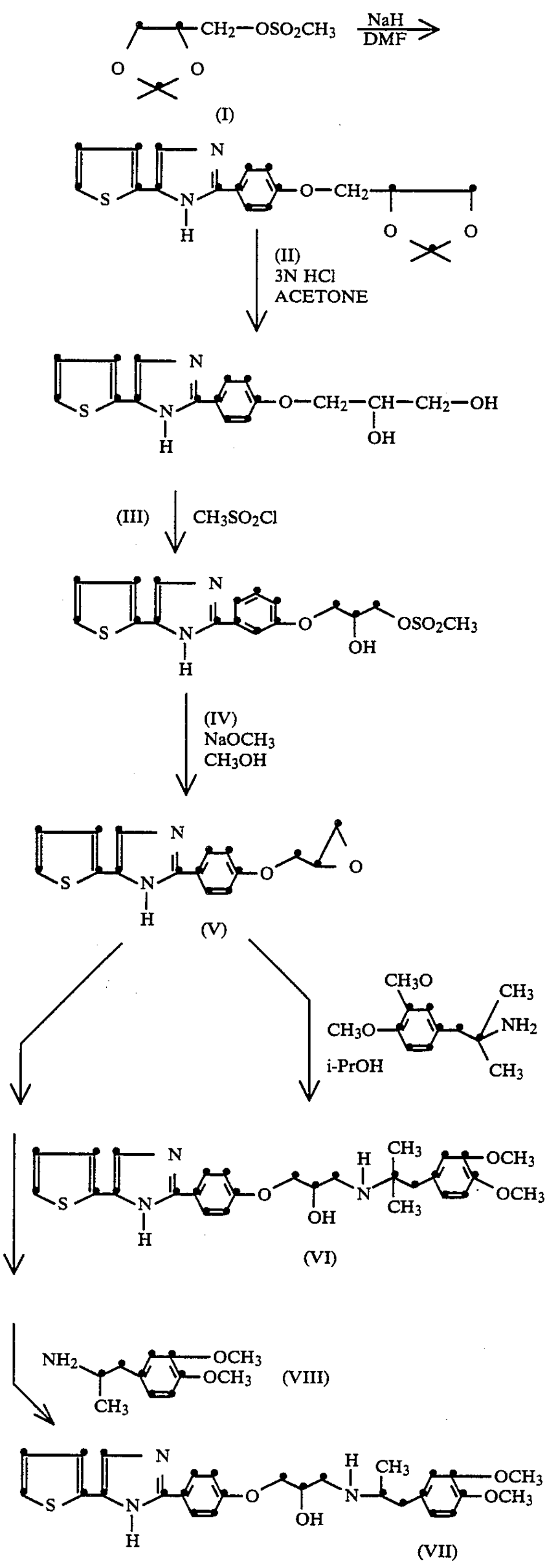

(a)

3-[p-[4-(2-Thienyl)-2-imidazolyl]phenoxy]-1,2-propanediol Acetonide, (II)

A solution of 2-(p-hydroxyphenyl)-4-(2-thienyl)-imidazole (19.5 g., 0.08 m.) in dimethylformamide (65 ml.) is added to a stirred suspension of sodium hydride (4.8 g., 0.10 m, 50% dispersion in mineral oil) in dimethylformamide (20 ml.) at 80° C. After stirring at 80° C. for 0.5 hours, a solution of 2,2-dimethyl-4-(hydroxymethyl)-1,3-dioxolane methanesulfonate, (I) (16.82 g., 0.08 m.) in dimethylformamide (20 ml.) is added rapidly and the mixture is stirred under nitrogen at 80° C. for 17 hours. The reaction mixture is poured into $H_2O$ (400 ml.) and extracted with ether (3×350 ml.). The combined extracts are washed with 5% NaOH solution (2×250 ml.) and with $H_2O$ (3×), dried, and the solvent is evaporated under reduced pressure to yield crude (II) (14.22 g.) which is used without further purification.

Using (R) I in place of I gave (R) II which was used without further purification.

(b)

3-[p-[4-(2-Thienyl)-2-imidazolyl]phenoxy]-1,2-propanediol, (III)

A mixture of 3-[p-[4-(2-thienyl)-2-imidazolyl]phenoxy]-1,2-propanediol acetonide (14.15 g., 0.04 m) in 3N HCl (80 ml.) and acetone (80 ml.) is refluxed for 0.5 hours. Acetone is removed under reduced pressure and the aqueous mixture is rendered alkaline with $K_2CO_3$. The solid is collected and dried in a vacuum oven at 60° C. to yield (III) (10.38 g., 82%, m.p. 197°-200° C.).

Similarly using (R)-II in place of II gave (R) III, mp 200°-205° which was used directly.

(c)

3-[p-[4-(2-Thienyl)-2-imidazolyl]phenoxy]-1,2-propanediol-1-methanesulfonate, (IV)

A mixture of 3-[p-[4-(2-thienyl)-2-imidazolyl]phenoxy]-1,2-propanediol (10.3 g., 0.033 m.), pyridine hydrochloride (4.28 g., 0.037 m.) and pyridine (65 ml.) is cooled in an ice bath and stirred while methanesulfonyl chloride (3.78 g., 0.033 m.) is added over 10 minutes. The mixture is stirred at room temperature for 1.5 hours, then a cold solution of $K_2CO_3$ (4.56 g., 0.033 m.) in $H_2O$ (22 ml) is added and the mixture is concentrated below 50° C. under high vacuum. The residue is chromatographed on silica gel, eluting with 10% MeOH-$CHCl_3$ to yield (IV) (4.52 g., 35%).

(d)

3-[p-[4-(2-thienyl)-2-imidazolyl]phenoxy]1,2-epoxypropane, (V)

A solution of 3-[p-[4-(2-thienyl)-2-imidazolyl]phenoxy]-1,2-propanediol-1-methanesulfonate (4.45 g., 0.011 m.) in methanol (40 ml.) and methylene chloride (40 ml.) is cooled in an ice bath while a solution of sodium methoxide (0.54 g., 0.010 m) in methanol (9 ml.) is added over 10 minutes with stirring. After stirring at 0° C. for 1.5 hours, $H_2O$ (165 ml.) is added and the organic layer is separated. The aqueous layer is extracted with $CH_2Cl_2$ (2×175 ml.) and the combined organic layers are dried and the solvent is concentrated under reduced pressure to yield (V) as an amorphous solid (3.37 g.).

(e)

2-[p-[[3-[2-(3,4-Dimethoxyphenyl)-2-methyl-2-propylamino]-2-hydroxypropoxy]]phenyl]-4-(2-thienyl-)imidazole, (VI)

A mixture of 3-[p-[4-(2-thienyl)-2-imidazolyl]phenoxy]-1,2-epoxy-propane (1.76 g., 0.0084 m.) and 3-(3,4-dimethoxyphenyl)-2-methylpropylamine in isopropanol (25 ml.) and methanol (5 ml.) is stirred at 70° C. for 16.5 hours. The solvent is evaporated under reduced pressure and the residue is chromatographed on silica gel, eluting with 10% MeOH—$CHCl_3$. The product is rechromatographed on silica gel, eluting with 3% MeOH—$CHCl_3$ saturated with $NH_3$ yielding 0.78 g. (18% ) of (VI) which is crystallized as the dihydrochloride salt from EtOH-MeOH-ether after treatment with decolorizing carbon (m.p. 241°-3° C.).

Anal. Calcd. for $C_{28}H_{33}N_3O_4S.2HCl.H_2O$: C, 56.18; H, 6.23; N, 7.02; Cl, 11.85. Found: C, 56.40; H, 6.15; N, 7.06; Cl, 11.76.

Starting with (R) III combining steps c,d and e and substituting 2-[3,4-dimethoxy-phenylethylamine for 3-(3,4-dimethoxyphenyl-2-methyl-2-propylamine gave (R) 2-{p-[[3-[2-(3,4-dimethoxyphenylethyl)amino]-2-hydroxypropoxy]]phenyl}-4-(2-thienyl)imidazole dihydrochloride m.p. 270°-272° C.

(f) 3-(3,4-Dimethoxyphenyl)-2-propylamine (VIII)

A mixture of 3,4-dimethoxyphenylactone (51.1 g., 0.26 m.) is dissolved in methanol (780 ml.), sodium cyanoborohydride (11.3 g., 0.18 m) is added and the mixture is stirred at room temperature for 67 hours. The reaction mixture is adjusted to pH 2 with concentrated HCl and the solvent is evaporated under reduced pressure. The residue is dissolved in $H_2O$ (250 ml.), the aqueous layer is extracted with ether (3X) and then rendered alkaline with KOH and extracted with $CH_2Cl_2$ (3X). After drying, the solvent is evaporated under reduced pressure and the product is distilled at 112°-5°/0.5 mm. to yield (VIII) (33.88 g., 67%).

(g)

2-[p-[[3-[2-(3,4-Dimethoxyphenyl)-2-propylamino]-2-hydroxypropoxy]]phenyl]-4-(2-thienyl)imidazole, (VII)

A mixture of 3-[p-[4-(2-thienyl)-2-imidazolyl]phenoxy]-1,2-epoxypropane (3.32 q., 0.011 m.) and 3-(3,4-dimethoxyphenyl)-2-propylamine (2.93 g., 0.015 m.) in isopropanol (30 ml.) and methanol (20 ml.) is stirred at 70° C. for 24 hours. The solvent is concentrated under reduced pressure and the residue is chromatographed on silica gel, eluting with 3% MeOH—$CHCl_3$ saturated with $NH_3$. The product (VII) is crystallized as a somewhat hygroscopic dihydrochloride salt from EtOH-ether after treatment with decolorizing carbon (m.p. 175°-9° C.).

Anal. Calcd. for $C_{27}H_{31}N_3O_4S.2HCl$: C, 57.24; H, 5.87; N, 7.42. Found: C, 57.26 & 57.10; H, 6.00 & 6.00; N, 7.57 & 7.51.

EXAMPLE M

Alternate Synthesis of 2-[p-[[3-(3,4-Dimethoxyphenyl)-2-propylamino]-2-hydroxypropoxy]]phenyl]-4-(2-thienyl)-imidazole, (III)

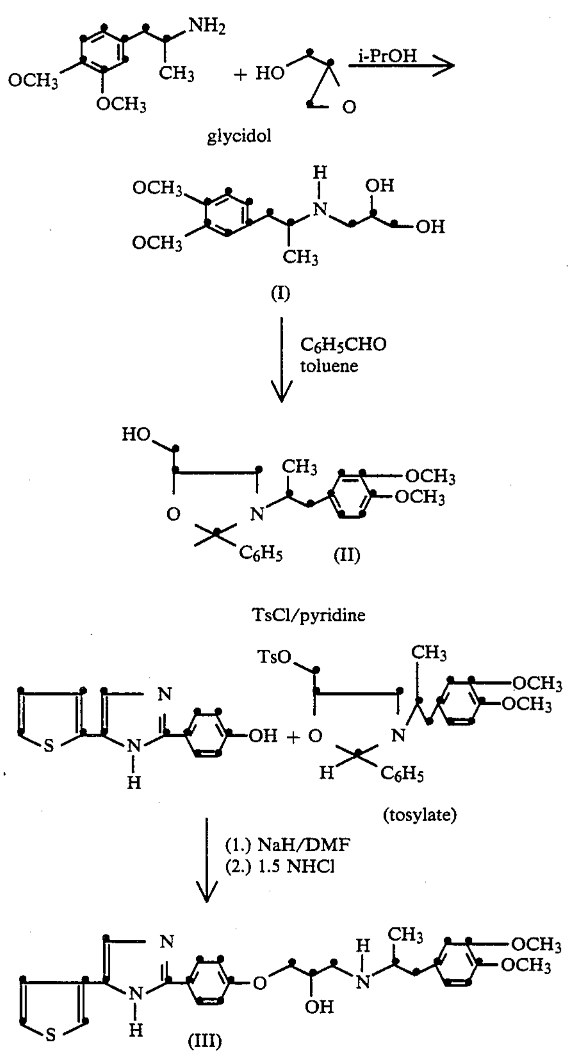

(a) 3-[3-(3,4-Dimethoxyphenyl)-2-propylamino]-1,2-propanediol, (I)

A solution of 3-(3,4-dimethoxyphenyl)-2-propylamine (20.0 g., 0.10 m.) in isopropanol (20 ml.) is heated to 50° C. while a solution of glycidol (5.0 g., 0.067 m.) in isopropanol (5 ml.) is added over 15 minutes. The mixture is stirred at 50° C. for 0.5 hours and then at 70° C. for 16 hours. The solvent is concentrated under reduced pressure and the residue is chromatographed on silica gel, eluting with 10% MeOH—$CHCl_3$ saturated with $NH_3$ to yield (I) weighing 14.37 g. (80%).

(b) 3-[3-(3,4-Dimethoxyphenyl-2-propyl]-5-hydroxymethyl-2-phenyloxazolidine, (II)

A mixture of 3-[3-(3,4-dimethoxyphenyl)-2-propylamino]-1,2-propanediol (14.3 g., 0.053 m.), benzaldehyde (12.7 g., 0.12 m.) and benzoic acid (0.3 g.) in toluene (45 ml.) is refluxed for 3 hours, collecting the water formed in a Dean-Stark trap. After washing with saturated $NaHCO_3$ solution and with $H_2O$ (2x), the solvent is distilled under reduced pressure. Excess benzaldehyde is distilled at 100° C. at 0.1 mm. The residue, (II) (16.88 g., 89%) is used without further purification in the next step.

(c) 2-[p-[[3-[3-(3,4-Dimethoxyphenyl)-2-propylamino]-2-hydroxypropoxy]]phenyl]-4-(2-thienyl) imidazole, (III)

A solution of 3-[3-(3,4-dimethoxyphenyl)-2-propylamino]-5-hydroxymethyl-2-phenyloxazolidine (11.08 g., 0.031 m.) in pyridine (12 ml.) is cooled to 10° C. and p-toluenesulfonyl chloride (5.91 g., 0.031 m.) is added over 30 minutes with stirring, keeping the temperature below 25° C. After stirring at 25° C. for 3 hours, a cold solution of $K_2CO_3$ (4.28 g., 0.031 m.) in $H_2O$ (28 ml.) is added and the mixture is extracted with $CHCl_3$ (3×55 ml.). The extracts are washed with $H_2O$, dried and concentrated under reduced pressure below 50° C., initially using water aspiration and finally high vacuum to yield the tosylate (16.21 g., 100%). Sodium hydride (1.39 g., 0.029 m, 50% dispersion in mineral oil) is added to a solution of 2-(p-hydroxyphenyl)-4-(2-thienyl)imidazole (7.00 g., 0.029 m.) in dimethylformamide (52 ml.) under nitrogen and the mixture is heated at 60° C. for 30 minutes. A solution of the tosylate (16.21 g., 0.031 m.) in dimethylformamide (45 ml.) is added and the mixture is heated at 120° C. for 20 hours. The solvent is distilled under reduced pressure, saturated $Na_2CO_3$ solution (100 ml.) is added and the mixture is extracted with ethyl acetate (2×125 ml.) and $CHCl_3$ (2×125 ml.). The combined organic layers are washed with $H_2O$, dried and concentrated under reduced pressure. The residue is heated on a steam bath for 1.5 hours in 1.5N HCl (280 ml.), cooled and extracted with ether (2×150 ml.). The acid layer is rendered alkaline with 20% NaOH solution and extracted with $CHCl_3$ (3×200 ml.). The solvent is concentrated under reduced pressure and the residue is chromatographed on silica gel, eluting with 5% MeOH—$CHCl_3$ saturated with $NH_3$. The product (III) is crystallized as the dihydrochloride salt from EtOH-ether (m.p. 170.5°–173.5° C.).

Preferred compounds which are prepared using the processes substantially as described above are tabulated below:

TABLE A

Compounds of the Formula

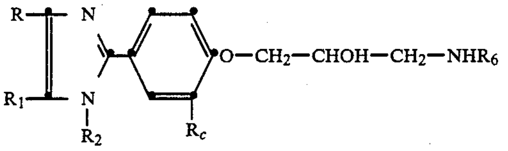

| R | $R_1$ | $R_2$ | $R_c$ | $R_6$ |
|---|---|---|---|---|
| H | 2-thienyl | H | H | $(CH_2)_2C_6H_5$ |
| H | 2-thienyl | H | H | $(CH_2)_2$—(3,4-di$OCH_3$—$C_6H_3$) |
| H | 2-thienyl | H | H | cyclopropyl |
| H | 2-thienyl | H | H | isopropyl |
| H | 2-thienyl | H | H | n-propyl |
| H | 2-thienyl | H | H | $C(CH_3)_2$—$CH_2$—(3,4-di$OCH_3$—$C_6H_3$) |
| H | 2-thienyl | H | H | $CH(CH_3)$—$CH_2$—(3,4-di$OCH_3$—$C_6H_3$) |
| H | 2-thienyl | H | H | t-butyl |
| H | $CH_3$ | H | H | $(CH_2)_2$—(3,4-di$OCH_3$—$C_6H_3$) |
| H | $CH_3$ | H | H | cyclopropyl |
| H | H | H | H | $(CH_2)_2$—(3,4-di$OCH_3$—$C_6H_3$) |
| H | H | H | H | cyclopropyl |
| H | H | $CH_3$ | H | $(CH_2)_2$—(3,4-di$OCH_3$—$C_6H_3$) |
| H | H | H | $OCH_3$ | $(CH_2)_2$—(3,4-di$OCH_3$—$C_6H_3$) |
| H | H | H | Br | $(CH_2)_2$—(3,4-di$OCH_3$—$C_6H_3$) |
| H | $CH_3$ | H | $OCH_3$ | $(CH_2)_2$—(3,4-di$OCH_3$—$C_6H_3$) |
| H | t-butyl | H | H | $(CH_2)_2$—(3,4-di$OCH_3$—$C_6H_3$) |
| H | isopropyl | H | H | $(CH_2)_2$—(3,4-di$OCH_3$—$C_6H_3$) |
| $C_1$-$C_6$alkyl | $CH_3$ | H | H | $(CH_2)_2$—(3,4-di$OCH_3$—$C_6H_3$) |
| $C_1$-$C_6$alkyl | $CH_3$ | H | $OCH_3$ | $(CH_2)_2$—(3,4-di$OCH_3$—$C_6H_3$) |
| halo | $CH_3$ | H | H | $(CH_2)_2$—(3,4-di$OCH_3$—$C_6H_3$) |
| halo | $CH_3$ | H | $OCH_3$ | $(CH_2)_2$—(3,4-di$OCH_3$—$C_6H_3$) |

Claims to the invention follow.

What is claimed is:

1. A compound having the formula:

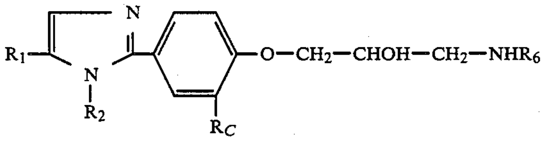

wherein $R_1$ *L is H, $CH_3$*, tert.butyl or isopropyl, $R_2$ is H or $CH_3$ $R_c$ is H, halo or $OCH_3$ and $R_6$ is

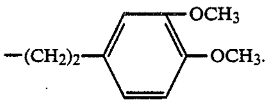

2. A compound of claim 1 wherein $R_2$ is H and $R_c$ is H, Br, Cl, F or $OCH_3$.

3. A compound having the formula

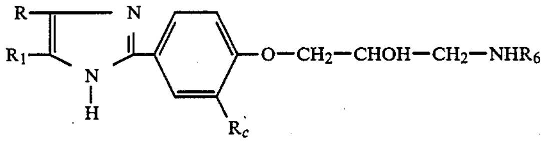

wherein R is $C_1$-$C_6$ alkyl or halo, $R_c$ is H, $OCH_3$, Br, Cl or F, $R_1$ is lower alkyl and $R_6$ is

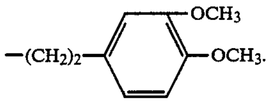

4. A compound of claim 3 wherein $R_1$ is $CH_3$.

5. A compound having the formula:

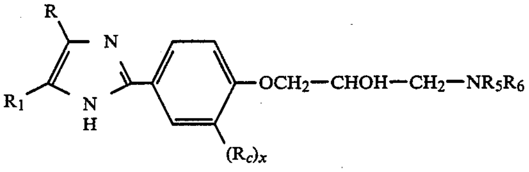

wherein R is hydrogen or an aromatic heterocyclic group selected from quinoline and those having 5-6 ring atoms, one to two of which is the hetero atom O, S, or N which heterocyclic group may be substituted on the carbon with 1 to 3 substituents selected from halo and lower alkyl and when the hetero atom is nitrogen may be substituted on the nitrogen with oxygen; $R_c$ is selected from halogen, $C_1$-$C_4$ linear or branched alkyl, $C_3$-$C_4$ cycloalkyl, $C_1$-$C_4$ alkoxy, hydroxy or cyano; $R_5$ is H; $R_6$ is $C_1$-$C_6$ linear, branched, or cyclic alkyl or substituted $C_1$-$C_6$ linear or branched alkyl wherein said substitutent is phenyl or lower alkoxy-substituted phenyl, x=0 or 1; and $R_1$ is phenyl or substituted phenyl wherein said substituent is $C_1$-$C_6$ alkyl, $C_1$-$C_6$ alkoxy, cyano, halo, nitro, amino, carboxy, hydroxy, —SH, sulfamoyl, $C_1$-$C_6$ alkylthio and phenyl.

6. A compound having the formula:

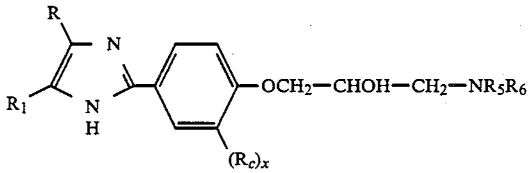

wherein R is hydrogen or an aromatic heterocyclic group selected from quinoline or those having 5-6 ring atoms, one to two of which are selected from the hetero atoms oxygen, sulfur, or nitrogen which heterocyclic group may be substituted on the carbon with 1 to 3 substituents selected from halo and lower alkyl and when the hetero atom is nitrogen may be substituted on the nitrogen with oxygen; $R_c$ is selected from halogen, $C_1$-$C_4$ linear or branched alkyl, $C_3$-$C_4$ cycloalkyl, $C_1$-$C_4$ alkoxy, hydroxy or cyano; $R_5$ is H; $R_6$ is $C_{1-6}$ linear, branched or cyclic alkyl or substituted $C_{1-6}$ linear, branched or cyclic alkyl wherein said substituent is phenyl or lower alkoxy-substituted phenyl, x is 0 or 1; and $R_1$ is phenyl, halophenyl or $C_{1-6}$ alkoxyphenyl.

7. A compound of claim 5 wherein $R_1$ is phenyl, halophenyl or $C_1$-$C_6$ alkoxyphenyl.

8. A compound of claim 7 wherein $R_6$ is cyclopropyl, t-butyl, isopropyl,

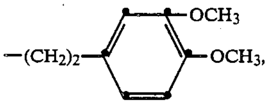

-continued

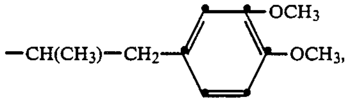

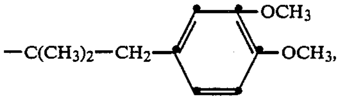

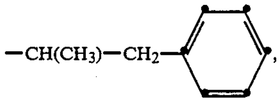
,
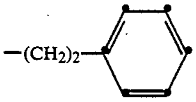

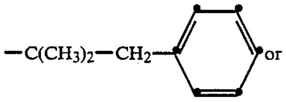
or
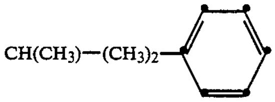

9. A compound of claim 8 wherein $R_1$ is p—$CH_3$—O—$C_6H_4$, p—Cl—$C_6H_4$, p—F—$C_6H_4$, pentafluorophenyl, phenyl or 3,4-diCl-$C_6H_3$.

10. A compound of claim 9 wherein $R_1$ is p—$CH_3$—O—$C_6H_4$ and $R_6$ is t-butyl.

11. The S-isomer of the claim 10 compound.

12. The R-isomer of the claim 10 compound.

13. The S or R isomer of the claim 7 compound.

14. S-2-[4-(3-tert-butylamino-2-hydropropoxy)-phenyl]-4-(4-methoxyphenyl)imidazole or a pharmacologically acceptable salt thereof.

15. 2-[4-(3-Tert-butylamino-2-hydroxypropoxy)-phenyl]-4-cyanoimidazole or a pharmacologically acceptable salt thereof.

* * * * *